(12) United States Patent
Kautz

(10) Patent No.: US 7,585,872 B2
(45) Date of Patent: *Sep. 8, 2009

(54) GUANIDINYL-SUBSTITUTED HYDROXY-6-PHENYLPHENANTHRIDINES AS EFFECTIVE PHOSPHODIESTERASE (PDE) 4 INHIBITORS

(75) Inventor: Ulrich Kautz, Allensbach (DE)

(73) Assignee: NYCOMED GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/589,082

(22) PCT Filed: Feb. 17, 2005

(86) PCT No.: PCT/EP2005/050708

§ 371 (c)(1),
(2), (4) Date: Sep. 5, 2006

(87) PCT Pub. No.: WO2005/077906

PCT Pub. Date: Aug. 25, 2005

(65) Prior Publication Data

US 2007/0167482 A1 Jul. 19, 2007

(30) Foreign Application Priority Data

Feb. 18, 2004 (EP) .................................. 04003592

(51) Int. Cl.
*A61K 31/473* (2006.01)
(52) U.S. Cl. ........................................ 514/298; 546/109
(58) Field of Classification Search ................. 546/101, 546/109; 514/298
See application file for complete search history.

(56) References Cited

U.S. PATENT DOCUMENTS

| 6,121,279 | A | 9/2000 | Gutterer |
| 6,127,378 | A | 10/2000 | Gutterer |
| 6,191,138 | B1 | 2/2001 | Gutterer |
| 6,306,869 | B1 | 10/2001 | Flockerzi |
| 6,410,551 | B1 | 6/2002 | Gutterer |
| 6,476,025 | B1 | 11/2002 | Gutterer |
| 7,329,676 | B2 * | 2/2008 | Kautz et al. .................. 514/298 |
| 2006/0116518 | A1 * | 6/2006 | Flockerzi et al. ............. 546/108 |

FOREIGN PATENT DOCUMENTS

| EP | 0 490 823 A1 | 6/1992 |
| WO | 97/28131 A1 | 8/1997 |
| WO | 97/35854 A1 | 10/1997 |
| WO | 99/05111 A1 | 2/1999 |
| WO | 99/05112 A1 | 2/1999 |
| WO | 99/05113 A1 | 2/1999 |
| WO | 99/57118 A1 | 11/1999 |
| WO | 00/42017 A1 | 7/2000 |
| WO | 00/42018 A1 | 7/2000 |
| WO | 00/42019 A1 | 7/2000 |
| WO | 00/42020 A1 | 7/2000 |
| WO | 00/42034 A1 | 7/2000 |
| WO | 02/05616 A1 | 1/2002 |
| WO | 02/06238 A1 | 1/2002 |
| WO | 02/06270 A1 | 1/2002 |
| WO | 02/066476 A1 | 8/2002 |
| WO | 2004/018431 A2 | 3/2004 |
| WO | 2004/019944 A1 | 3/2004 |
| WO | 2004/019945 A1 | 3/2004 |
| WO | 2005/084104 A2 | 9/2005 |
| WO | 2005/085203 A1 | 9/2005 |
| WO | 2005/085225 A1 | 9/2005 |
| WO | 2005/087744 A1 | 9/2005 |
| WO | 2005/087745 A1 | 9/2005 |
| WO | 2005/090311 A1 | 9/2005 |
| WO | 2006/092422 A1 | 9/2006 |

OTHER PUBLICATIONS

"Souness, J.E., "Immunosuppressive and anti-inflammatory effects of cyclic AMP phosphodiesterase (PDE) type 4 inhibitors". *Immunopharmacology*, vol. 47, p. 127-162, 2000".
"Dyke, H.J., "Update on the therapeutic potential of PDE4 inhibitors". *Expert Opinion on Investigational Drugs*, vol. 11, No. 1, p. 1-13, 2002".
Montana, J., "Chapter 5. Phosphodiesterase 4 Inhibitors". *Annual Reports Med Chem*, vol. 36, p. 47-56, 2001.
"Schmidt, B.J., "The phosphodieseterase 4 inhibitor roflumilast is effective in the treatment of allergic rhinitis". *Allergy Clin Immunol*, vol. 108, p. 530-536, 2001".

* cited by examiner

*Primary Examiner*—Rita J Desai
*Assistant Examiner*—David K O'Dell
(74) *Attorney, Agent, or Firm*—The Nath Law Group; Joshua B. Goldberg; Sheldon M. McGee

(57) ABSTRACT

The compounds of a certain formula (1),

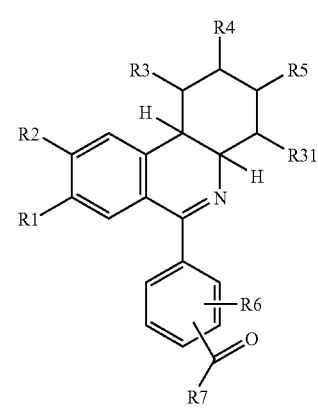

in which R1, R2, R3, R31, R4, R5, R6 and R7 have the meanings as given in the description, are novel effective PDE4 inhibitors.

10 Claims, No Drawings

GUANIDINYL-SUBSTITUTED HYDROXY-6-PHENYLPHENANTHRIDINES AS EFFECTIVE PHOSPHODIESTERASE (PDE) 4 INHIBITORS

This application was filed under 35 U.S.C. 371 as a national stage of PCT/EP2005/050708, filed Feb. 17, 2005.

FIELD OF APPLICATION OF THE INVENTION

The invention relates to novel guanidinyl-substituted hydroxy-6-phenylphenanthridine derivatives, which are used in the pharmaceutical industry for the production of pharmaceutical compositions.

KNOWN TECHNICAL BACKGROUND

The International Patent applications WO99/57118 and WO02/05616 describe 6-phenylphenanthridines as PDE4 inhibitors.

In the International Patent application WO99/05112 substituted 6-alkylphenanthridines are described as bronchial therapeutics.

In the International Patent application WO02/066476 benzonaphthyridine derivatives are described which have a guanidyl substituent.

In the European Patent application EP 0490823 dihydroisoquinoline derivatives are described which are useful in the treatment of asthma.

The International Patent application WO2004/018431 discloses 6-phenylphenanthridines as PDE4 inhibitors.

The International Patent application WO02/066476 discloses 6-phenylbenzonaphthyridines as PDE4 inhibitors.

The U.S. Pat. No. 6,476,0251 discloses 6-phenylphenanthridines as PDE4 inhibitors.

The U.S. Pat. No. 6,306,8691 discloses benzonaphthyridine N-oxides as PDE4 inhibitors.

The International Patent applications WO2004/019944 and WO2004/019945 disclose hydroxy-substituted 6-phenylphenanthridines as PDE4 inhibitors.

DESCRIPTION OF THE INVENTION

It has now been found that the novel guanidinyl-substituted 2- or 3-hydroxy-6-phenylphenanthridines described in greater detail below differ from the previously known compounds by unanticipated and sophisticated structural alterations and have surprising and particularly advantageous properties.

The invention thus relates to compounds of formula 1, (1)

in which

R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, either, in a first embodiment (embodiment a) according to the present invention, R4 is —O—R41, in which R41 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl, and R5 is hydrogen or 1-4C-alkyl, or, in a second embodiment (embodiment b) according to the present invention, R4 is hydrogen or 1-4C-alkyl, and R5 is —O—R51, in which R51 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl, R6 is hydrogen, halogen, nitro, 1-4C-alkyl, trifluoromethyl or 1-4C-alkoxy, R7 is a radical of formulae (a), (b), (c) or (d)

(a)

(b)

(c)

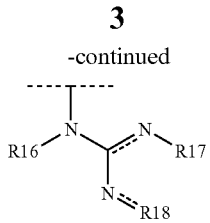

(d)

in which if R7 is a radical of the formula (b), either
R8, R9, R10 and R11 independently of one another are hydrogen, 1-7C-alkyl, 3-7C-cycloalkyl, 3-7C-cycloalkylmethyl, cyano, hydroxy-2-4C-alkyl, 1-4C-alkoxy-2-4C-alkyl or R28, or
R8 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, R9 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and R10 and R11, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, tetrahydro-6,7-dimethoxyisoquinolin-2-yl, 3,5-dimethyl-pyrazol-1-yl, pyrazol-1-yl, 2,6-dimethyl-morpholin-4-yl, 2,6-dimethyl-piperidin-1-yl, 4-benzyl-piperidin-1-yl, thiomorpholin-4-yl or 1H-1,2,4-triazol-1-yl radical, or a piperazin-1-yl radical substituted in 4-position by R19, or
R8 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, R9 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, R10 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and R11 is Aryl1, naphthyl, phenyl, phenyl substituted by R20 and/or R21, phenyl-1-4C-alkyl or phenyl-1-4C-alkyl substituted by R22 and R23, in which if R7 is a radical of the formula (c), either
R12, R13, R14 and R15 independently of one another are hydrogen, 1-7C-alkyl, 3-7C-cycloalkyl, 3-7C-cycloalkylmethyl, hydroxy-2-4C-alkyl, 1-4C-alkoxy-2-4C-alkyl or R28, or
R12 and R13 independently of one another are hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and R14 and R15, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, tetrahydro-6,7-dimethoxyisoquinolin-2-yl, 3,5-dimethyl-pyrazol-1-yl, pyrazol-1-yl, 2,6-dimethyl-morpholin-4-yl, 2,6-dimethyl-piperidin-1-yl, 4-benzyl-piperidin-1-yl, thiomorpholin-4-yl or 1H-1,2,4-triazol-1-yl radical, or a piperazin-1-yl radical substituted in 4-position by R19, or
R12 and R13, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl, 2,6-dimethyl-piperidin-1-yl, 4-benzyl-piperidin-1-yl or thiomorpholin-4-yl radical, and R14 and R15, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl, 2,6-dimethyl-piperidin-1-yl, 4-benzyl-piperidin-1-yl or thiomorpholin-4-yl radical, or
R12 and R15 independently of one another are hydrogen or 1-4C-alkyl, and R13 and R14, together and with inclusion of the N—C(═)—N structure to which they are bonded, are a hexahydropyrimidin-2-ylidene or imidazolidin-2-ylidene radical, in which if R7 is a radical of the formula (d),
R16 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and R17 and R18, together and with inclusion of the N—C(═)—N structure to which they are bonded are Aryl2, Aryl1 is 4-methylthiazol-2-yl, benzimidazol-2-yl, 5-nitrobenzimidazol-2-yl, 5-chlorobenzimidazol-2-yl, 5-methylbenzimidazol-2-yl, 4-methylquinazolin-2-yl, benzothiazol-2-yl, benzoxazol-2-yl or pyrimidin-2-yl, Aryl2 is 1-methyl-4-oxo-4,5-dihydro-1H-imidazol-2-yl, imidazol-2-yl, 4,5-dicyano-imidazol-2-yl, 4-methyl-imidazol-2-yl, 4-ethyl-benzimidazol-2-yl, 4-acetyl-imidazol-2-yl, 1H-[1,2,4]triazol-3-yl, benzimidazol-2-yl, 1-methyl-benzimidazol-2-yl, 1-ethyl-benzimidazol-2-yl, 5,6-dimethylbenzimidazol-2-yl, purin-8-yl, 6-amino-7-methyl-7H-purine-8-yl, 1,6-dimethylimidazo[4,5-b]pyridin-2-yl, 1,5,6-trimethylimidazo[4,5-b]pyridin-2-yl, 1,3-dimethyl-3,7-dihydro-1H-purine-2,6-dione-8-yl, 7-ethyl-3-methyl-3,7-dihydro-purine-2,6-dione-8-yl, 1,3,7-trimethyl-3,7-dihydro-purine-2,6-dione-8-yl, thiadiazolyl, 1,4-dihydrotetrazol-5-yl, 1H-[1,2,4]triazol-3-yl, 1,3-dihydrobenzimidazol-5-yl, 1H-tetrazol-5-yl, pyrimidin-2-yl or 4,6-dimethyl-pyrimidin-2-yl, R19 is 1-4C-alkyl, formyl, 3-7C-cycloalkyl, 3-7C-cycloalkylmethyl, 1-4C-alkoxycarbonyl-1-4C-alkyl, 1-4C-alkylcarbonyl, hydroxy-2-4C-alkyl, 1-4C-alkoxy-2-4C-alkyl, hydroxy-2-4C-alkoxy-2-4C-alkyl, 1-4C-alkoxy-2-4C-alkoxy-2-4C-alkyl, phenyl, phenyl substituted by R24 and/or R25, [benzo(1,3)dioxol]-5-ylmethyl, phenyl-1-4C-alkyl or phenyl-1-4C-alkyl substituted in the phenyl moiety by R26 and/or R27, R20 is halogen, nitro, carboxyl, 1-4C-alkyl, trifluoromethyl or 1-4C-alkoxy, R21 is halogen, 1-4C-alkyl or 1-4C-alkoxy, R22 is halogen, nitro, carboxyl, 1-4C-alkyl, trifluoromethyl or 1-4C-alkoxy, R23 is halogen, 1-4C-alkyl or 1-4C-alkoxy, R24 is halogen, nitro, carboxyl, 1-4C-alkyl, 1-4C-alkylcarbonyl, trifluoromethyl or 1-4C-alkoxy, R25 is halogen, 1-4C-alkyl or 1-4C-alkoxy, R26 is halogen, nitro, carboxyl, 1-4C-alkyl, trifluoromethyl or 1-4C-alkoxy, R27 is halogen, 1-4C-alkyl or 1-4C-alkoxy, R28 is R29(R30)N-2-4C-alkyl wherein R29 and R30, together and including the nitrogen atom to which both are bonded, are a pyrrolidin-1-yl, piperidin-1-yl, piperazin-1-yl, 4-(1-4C-alkyl-)piperazin-1-yl, azepan-1yl, azocan-1-yl, azonan-1-yl, azecan-1-yl, tetrahydroisoquinolin-2-yl, tetrahydro-6,7-dimethoxyisoquinolin-2-yl, 3,5-dimethyl-pyrazol-1-yl, pyrazol-1-yl, morpholin-4-yl, 2,6-dimethyl-morpholinyl, 2,6-dimethyl-piperidin-1-yl, 4-benzyl-piperidin-1-yl, thiomorpholin-4-yl or 1H-1,2,4-triazol-1-yl radical, the salts of these compounds, as well as the N-oxides, enantiomers, E/Z isomers and tautomers of these compounds and their salts.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, propyl, isopropyl and, preferably, the ethyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3-7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1-4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned. In this context, "predominantly" means that more than half of the hydrogen atoms of the 1-4C-alkoxy groups are replaced by fluorine atoms.

1-2C-Alkylenedioxy represents, for example, the methylenedioxy (—O—$CH_2$—O—) or the ethylenedioxy (—O—$CH_2$—$CH_2$—O—) radical.

If R3 and R31 together have the meaning 1-C-alkylene, the positions 1 and 4 in compounds of the formula 1 are linked to one another by a 1-4C-alkylene bridge, 1-4C-alkylene representing straight-chain or branched alkylene radicals having 1 to 4 carbon atoms. Examples which may be mentioned are the radicals methylene [—$CH_2$—], ethylene [—$CH_2$—$CH_2$—], trimethylene [—$CH_2$—$CH_2$—$CH_2$—], 1,2-dimethylethylene [—CH($CH_3$)—CH($CH_3$)—] and isopropylidene [—C($CH_3$)$_2$—].

Halogen within the meaning of the invention is fluorine, chlorine or bromine.

1-7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radical.

3-7C-Cycloalkyl represents the cyclopropyl, cyclobutyl, cyclopentyl, cyclohexyl or cycloheptyl radical.

3-7C-Cycloalkylmethyl represents a methyl radical which is substituted by one of the above-mentioned 3-7C-cycloalkyl radicals. Examples which may be mentioned are the cycloalkylmethyl radicals cyclopropylmethyl, cyclobutylmethyl and cyclopentylmethyl.

Hydroxy-2-4C-alkyl represents 2-4C-alkyl radicals which are substituted by a hydroxyl group. Examples which may be mentioned are the 2-hydroxyethyl and the 3-hydroxypropyl radicals.

An example which may be mentioned for a hydroxy-2-4C-alkoxy-2-4C-alkyl radical is the (2-hydroxyethoxy)ethyl radical.

An example of a 1-4C-alkoxy-2-4C-alkoxy-2-4C-alkyl radical is the (2-methoxyethoxy)ethyl radical.

1-4C-Alkylcarbonyl is a carbonyl group to which one of the abovementioned 1-4C-alkyl radicals is bonded. An example is the acetyl radical [$CH_3$C(O)—].

1-4C-Alkoxycarbonyl is a carbonyl group to which one of the abovementioned 1-4C-alkoxy radicals is bonded. Examples are the methoxycarbonyl [$CH_3$O—C(O)—] and the ethoxycarbonyl [$CH_3CH_2$O—C(O)—] radical.

1-4C-Alkoxycarbonyl-1-4C-alkyl stands for one of the abovementioned 1-4C-alkyl radicals, which is substituted by one of the abovementioned 1-4C-alkoxycarbonyl radicals. An example is the ethoxycarbonylmethyl radical [$CH_3CH_2$OC(O)$CH_2$—].

1-4C-Alkoxy-2-4C-alkyl represents a 2-4C-alkyl radical, which is substituted by one of the abovementioned 1-4C-alkoxy radicals. Examples which may be mentioned are the methoxyethyl and the ethoxyethyl radical.

Phenyl-1-4C-alkyl radicals stand for one of the abovementioned 1-4C-alkyl radicals substituted by an phenyl group. Examples which may be mentioned are the phenylethyl and the benzyl radical.

R29(R30)N-2-4C-alkyl radicals stand for one of the abovementioned 2-4C-radicals substituted by an R29(R30)N—group. Examples which may be mentioned are morpholin-4-ylethyl and the thiomorpholin-4-ylethyl radicals.

"N-oxides of these compounds" stands for any single or multiple N-oxide(s), which can be formed starting from the compounds of formula 1, as well as any mixtures of the single or multiple N-oxides in any mixing ratio. Preferred are the single N-oxides at the nitrogen atom in 5-position of the phenanthridine ring system.

In the formulae (a), (b), (c) or (d) the horizontal dotted lines indicate

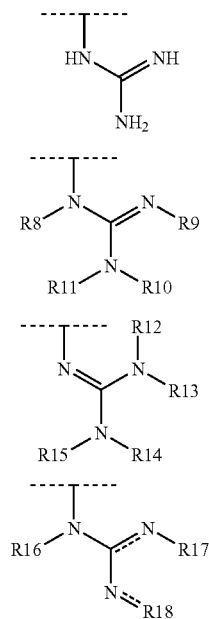

that R7 is bonded to the carbonyl group in formula 1 via the bond that bears the horizontal dotted line. The additional dotted lines in formula (d) indicate that there can be in the indicated positions a single or a double bond.

The substituents R6 and —C(O)R7 of the compounds of the formula 1 can be attached in the ortho, meta or para position with respect to the binding position in which the 6-phenyl ring is bonded to the phenanthridine ring system. Preference is given to compounds of the formula 1, in which R6 is hydrogen and —C(O)R7 is attached in the meta or in the para position, whereby in a special embodiment R6 is hydrogen and —C(O)R7 is attached in the para position.

Suitable salts of compounds of the formula 1—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand salts with bases are also suitable. Examples of salts with bases which may be mentioned are alkali metal (lithium, sodium, potassium) or calcium, aluminum, magnesium or titanium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

It is known to the person skilled in the art that the compounds according to the invention and their salts, for example when they are isolated in crystalline form, may comprise varying amounts of solvents. Accordingly, the invention also embraces all solvates and in particular all hydrates of the compounds of the formula 1, and also all solvates and in particular all hydrates of the salts of the compounds of the formula 1.

Compounds of the formula 1 to be emphasized are those in which

R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, either, in a first embodiment (embodiment a) according to the present invention, R4 is —O—R41, in which R41 is hydrogen or 1-7C-alkylcarbonyl, and R5 is hydrogen, or, in a second embodiment (embodiment b) according to the present invention, R4 is hydrogen, and R5 is —O—R51, in which R51 is hydrogen or 1-7C-alkylcarbonyl, R6 is hydrogen, halogen, nitro, 1-4C-alkyl, trifluoromethyl or 1-4C-alkoxy, R7 is a radical of formulae (a), (b), (c) or (d)

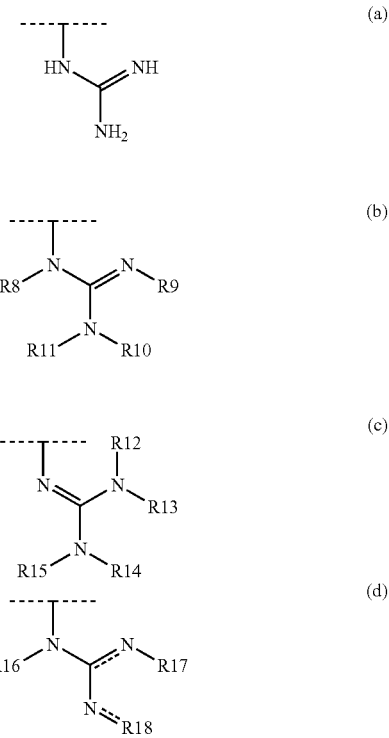

in which if R7 is a radical of the formula (b), either
R8, R9, R10 and R11 independently of one another are hydrogen, 1-7C-alkyl, 3-7C-cycloalkyl, 3-7C-cycloalkylmethyl or hydroxy-2-4C-alkyl, or
R8 is hydrogen, 1-7C-alkyl, 3-7C-cycloalkyl, 3-7C-cycloalkylmethyl or hydroxy-2-4C-alkyl,
R9 is hydrogen, 1-7C-alkyl, 3-7C-cycloalkyl, 3-7C-cycloalkylmethyl, hydroxy-2-4C-alkyl, and
R10 and R11, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, 3,5-dimethyl-pyrazol-1-yl, pyrazol-1-yl, 2,6-dimethyl-morpholin-4-yl, 2,6-dimethyl-piperidin-1-yl, thiomorpholin-4-yl or 1H-1,2,4-triazol-1-yl radical, or a piperazin-1-yl radical substituted in 4-position by R19, or
R8 is hydrogen, 1-7C-alkyl, 3-7C-cycloalkyl, 3-7C-cycloalkylmethyl or hydroxy-2-4C-alkyl,
R9 is hydrogen, 1-7C-alkyl, 3-7C-cycloalkyl, 3-7C-cycloalkylmethyl or hydroxy-2-4C-alkyl,
R10 is hydrogen, 1-7C-alkyl, 3-7C-cycloalkyl, 3-7C-cycloalkylmethyl or hydroxy-2-4C-alkyl, and
R11 is Aryl1, naphthyl, phenyl, phenyl substituted by R20 and/or R21, phenyl-1-4C-alkyl or phenyl-1-4C-alkyl substituted by R22 and R23, in which if R7 is a radical of the formula (c), either
R12, R13, R14 and R15 independently of one another are hydrogen, 1-7C-alkyl, 3-7C-cycloalkyl, 3-7C-cycloalkylmethyl or hydroxy-2-4C-alkyl, or
R12 and R13 independently of one another are hydrogen, 1-7C-alkyl, 3-7C-cycloalkyl, 3-7C-cycloalkylmethyl or hydroxy-2-4C-alkyl, and
R14 and R15, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, 3,5-dimethyl-pyrazol-1-yl, pyrazol-1-yl, 2,6-dimethyl-morpholin-4-yl, 2,6-dimethyl-piperidin-1-yl, thiomorpholin-4-yl or 1H-1,2,4-triazol-1-yl radical, or a piperazin-1-yl radical substituted in 4-position by R19, or
R12 and R13, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl, 2,6-dimethyl-piperidin-1-yl or thiomorpholin-4-yl radical, and
R14 and R15, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl, 2,6-dimethyl-piperidin-1-yl or thiomorpholin-4-yl radical, or
R12 and R15 independently of one another are hydrogen or 1-4C-alkyl, and
R13 and R14, together and with inclusion of the N—C(=)—N structure to which they are bonded, are a hexahydropyrimidin-2-ylidene or imidazolidin-2-ylidene radical, in which if R7 is a radical of the formula (d),
R16 is hydrogen, 1-7C-alkyl, 3-7C-cycloalkyl, 3-7C-cycloalkylmethyl or hydroxy-2-4C-alkyl, and
R17 and R18, together and with inclusion of the N—C(=)—N structure to which they are bonded are Aryl2,
Aryl1 is 4-methylthiazol-2-yl, benzimidazol-2-yl, 5-nitrobenzimidazol-2-yl, 5-chlorobenzimidazol-2-yl, 5-methylbenzimidazol-2-yl, 4-methylquinazolin-2-yl, benzothiazol-2-yl, benzoxazol-2-yl or pyrimidin-2-yl,
Aryl2 is 1-methyl-4-oxo-4,5-dihydro-1H-imidazol-2-yl, imidazol-2-yl, 4,5-dicyano-imidazol-2-yl, 4-methyl-imidazol-2-yl, 4-ethyl-benzimidazol-2-yl, 4-acetyl-imidazol-2-yl, 1H-[1,2,4]triazol-3-yl, benzimidazol-2-yl, 1-methyl-benzimidazol-2-yl, 1-ethyl-benzimidazol-2-yl, 5,6-dimethylbenzimidazol-2-yl, purin-8-yl, 6-amino-7-methyl-7H-purine-8-yl, 1,6-dimethylimidazo[4,5-b]pyridin-2-yl, 1,5,6-trimethylimidazo[4,5-b]pyridin-2-yl, 1,3-dimethyl-3,7-dihydro-1H-purine-2,6-dione-8-yl, 7-ethyl-3-methyl-3,7-dihydro-purine-2,6-dione-8-yl, 1,3,7-trimethyl-3,7-dihydro-purine-2,6-dione-8-yl, thiadiazolyl, 1,4-dihydrotetrazol-5-yl, 1H-[1,2,4]triazol-3-yl, 1,3-dihydrobenzimidazol-5-yl, 1H-tetrazol-5-yl, pyrimidin-2-yl or 4,6-dimethyl-pyrimidin-2-yl,
R19 is 1-4C-alkyl, formyl, 1-4C-alkylcarbonyl, 2-hydroxyethyl, phenyl, phenyl substituted by R24 and/or R25, phenyl-1-4C-alkyl or phenyl-1-4C-alkyl substituted in the phenyl moiety by R26 and/or R27,
R20 is halogen, nitro, carboxyl, 1-4C-alkyl, trifluoromethyl or 1-4C-alkoxy,
R21 is halogen, 1-4C-alkyl or 1-4C-alkoxy,
R22 is halogen, nitro, carboxyl, 1-4C-alkyl, trifluoromethyl or 1-4C-alkoxy,
R23 is halogen, 1-4C-alkyl or 1-4C-alkoxy,
R24 is halogen, nitro, carboxyl, 1-4C-alkyl, trifluoromethyl or 1-4C-alkoxy,
R25 is halogen, 1-4C-alkyl or 1-4C-alkoxy,
R26 is halogen, nitro, carboxyl, 1-4C-alkyl, trifluoromethyl or 1-4C-alkoxy,
R27 is halogen, 1-4C-alkyl or 1-4C-alkoxy, the salts of these compounds, as well as the N-oxides, enantiomers, E/Z isomers and tautomers of these compounds and their salts.

Compounds of the formula 1 to be in particular emphasized are those in which
R1 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R2 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R3 is hydrogen,
R31 is hydrogen, either, in a first embodiment (embodiment a) according to the present invention,
R4 is —O—R41, in which
R41 is hydrogen or 1-4C-alkylcarbonyl, and
R5 is hydrogen, or, in a second embodiment (embodiment b) according to the present invention, R4 is hydrogen, and
R5 is —O—R51, in which
R51 is hydrogen or 1-4C-alkylcarbonyl,
R6 is hydrogen, halogen, nitro, 1-4C-alkyl, trifluoromethyl or 1-4C-alkoxy,
R7 is a radical of formulae (a), (b), (c) or (d)

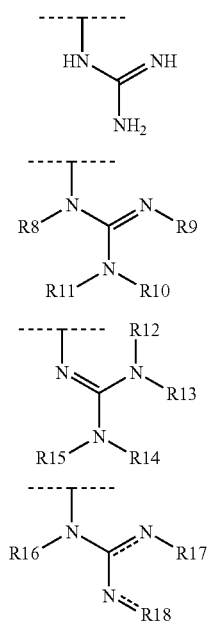

in which
if R7 is a radical of the formula (b),
either
R8 is hydrogen, and
R9, R10 and R11 independently of one another are hydrogen, 1-4C-alkyl, 3-7C-cycloalkyl or 3-7C-cycloalkylmethyl, or
R8 is hydrogen,
R9 is hydrogen, 1-4C-alkyl, 3-7C-cycloalkyl or 3-7C-cycloalkylmethyl, and
R10 and R11, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, 3,5-dimethyl-pyrazol-1-yl, pyrazol-1-yl, 2,6-dimethyl-morpholin-4-yl or 2,6-dimethyl-piperidin-1-yl radical, or a piperazin-1-yl radical substituted in 4-position by R19, or
R8 is hydrogen,
R9 is hydrogen, 1-7C-alkyl, 3-7C-cycloalkyl or 3-7C-cycloalkylmethyl,
R10 is hydrogen, 1-7C-alkyl, 3-7C-cycloalkyl or 3-7C-cycloalkylmethyl, and
R11 is Aryl1, naphthyl, phenyl, phenyl substituted by R20 and/or R21, phenyl-1-4C-alkyl or phenyl-1-4C-alkyl substituted by R22 and R23, in which
if R7 is a radical of the formula (c),
either
R12, R13, R14 and R15 independently of one another are hydrogen, 1-4C-alkyl, 3-7C-cycloalkyl or 3-7C-cycloalkylmethyl, or
R12 and R13 independently of one another are hydrogen, 1-4C-alkyl, 3-7C-cycloalkyl or 3-7C-cycloalkylmethyl, and
R14 and R15, together and including the nitrogen atom to which both are bonded, are a pyrrolidin-1-yl, piperidin-1-yl, azepan-1-yl, azocan-1-yl, azonan-1-yl, azecan-1-yl, morpholin-4-yl, tetrahydroisoquinolin-2-yl, 3,5-dimethyl-pyrazol-1-yl, pyrazol-1-yl, 2,6-dimethyl-morpholin-4-yl or 2,6-dimethyl-piperidin-1-yl radical, or a piperazin-1-yl radical substituted in 4-position by R19, or
R12 and R13, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl or 2,6-dimethyl-piperidin-1-yl radical, and
R14 and R15, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl or 2,6-dimethyl-piperidin-1-yl radical, or
R12 and R15 independently of one another are hydrogen or 1-4C-alkyl, and
R13 and R14, together and with inclusion of the N—C(=)—N structure to which they are bonded, are a hexahydropyrimidin-2-ylidene or imidazolidin-2-ylidene radical, in which
if R7 is a radical of the formula (d),
R16 is hydrogen, and
R17 and R18, together and with inclusion of the N—C(=)—N structure to which they are bonded are Aryl2,
Aryl1 is 4-methylthiazol-2-yl, benzimidazol-2-yl, 5-nitrobenzimidazol-2-yl, 5-chlorobenzimidazol-2-yl, 5-methylbenzimidazol-2-yl, benzothiazol-2-yl or benzoxazol-2-yl,
Aryl2 is 1-methyl-4-oxo-4,5-dihydro-1H-imidazol-2-yl, imidazol-2-yl, 4,5-dicyano-imidazol-2-yl, 4-methyl-imidazol-2-yl, 4-ethyl-benzimidazol-2-yl, 4-acetyl-imidazol-2-yl, 1H-[1,2,4]triazol-3-yl, benzimidazol-2-yl, 1-methyl-benzimidazol-2-yl, 1-ethyl-benzimidazol-2-yl, 5,6-dimethylbenzimidazol-2-yl, purin-8-yl, 6-amino-7-methyl-7H-purine-8-yl, 1,6-dimethylimidazo[4,5-b]pyridin-2-yl, 1,5,6-trimethylimidazo[4,5-b]pyridin-2-yl, 1,3-dimethyl-3,7-dihydro-1H-purine-2,6-dione-8-yl, 7-ethyl-3-methyl-3,7-dihydro-purine-2,6-dione-8-yl, 1,3,7-trimethyl-3,7-dihydro-purine-2,6-dione-8-yl or 1H-[1,2,4]triazol-3-yl,
R19 is 1-4C-alkyl, formyl, 1-4C-alkylcarbonyl, 2-hydroxyethyl, phenyl, phenyl substituted by R24 and/or R25, phenyl-1-4C-alkyl or phenyl-1-4C-alkyl substituted in the phenyl moiety by R26 and/or R27,
R20 is halogen, nitro, 1-4C-alkyl or 1-4C-alkoxy,
R21 is halogen, 1-4C-alkyl or 1-4C-alkoxy, R22 is halogen, nitro, 1-4C-alkyl or 1-4C-alkoxy,
R23 is halogen, 1-4C-alkyl or 1-4C-alkoxy,
R24 is halogen, nitro, carboxyl, 1-4C-alkyl or 1-4C-alkoxy,
R25 is halogen, 1-4C-alkyl or 1-4C-alkoxy,
R26 is halogen, nitro, 1-4C-alkyl or 1-4C-alkoxy,
R27 is halogen, 1-4C-alkyl or 1-4C-alkoxy, the salts of these compounds, as well as the N-oxides, enantiomers, E/Z isomers and tautomers of these compounds and their salts.

Compounds of the formula 1 to be in more particular emphasized are those in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy,
R3 is hydrogen,
R31 is hydrogen, either, in a first embodiment (embodiment a) according to the present invention,
R4 is —O—R41, in which
R41 is hydrogen or 1C-alkylcarbonyl, and
R5 is hydrogen, or, in a second embodiment (embodiment b) according to the present invention,
R4 is hydrogen, and
R5 is —O—R51, in which
R51 is hydrogen or 1-4C-alkylcarbonyl,
R6 is hydrogen,
R7 is a radical of formulae (a), (b), (c) or (d)

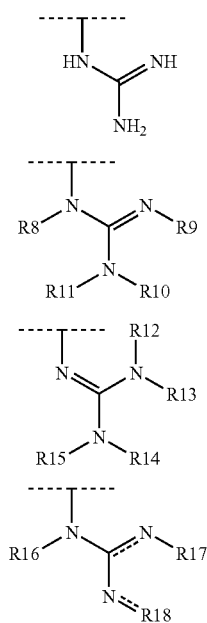

in which
if R7 is a radical of the formula (b),
either
R8 is hydrogen, and
R9 is hydrogen,
R10 is hydrogen or 1-4C-alkyl,
R11 is hydrogen or 1-4C-alkyl,
where at least one of the radicals R10 or R11 is not hydrogen, or
R8 is hydrogen,
R9 is hydrogen,
R10 and R11, together and including the nitrogen atom to which both are bonded, are a pyrrolidin-1-yl, piperidin-1-yl, azepan-1-yl, azocan-1-yl, azonan-1-yl, morpholin-4-yl, tetrahydroisoquinolin-2-yl or 3,5-dimethyl-pyrazol-1-yl radical, or a piperazin-1-yl radical substituted in 4-position by R19, or
R8 is hydrogen,
R9 is hydrogen,
R10 is hydrogen or 1-4C-alkyl, and
R11 is Aryl1, naphthyl, phenyl or phenyl substituted by R20, in which
if R7 is a radical of the formula (c),
either
R12 is hydrogen or 1-4C-alkyl,
R13 is hydrogen or 1-4C-alkyl,
R14 is hydrogen or 1-4C-alkyl, and
R15 is hydrogen, 1-4C-alkyl or 3-7C-cycloalkyl,
where at least one of the radicals R12, R13, R14 and R15 is not hydrogen, or
R12 is hydrogen or 1-4C-alkyl,
R13 is hydrogen or 1-4C-alkyl, and
R14 and R15, together and including the nitrogen atom to which both are bonded, are a pyrrolidin-1-yl, piperidin-1-yl, azepan-1-yl, azocan-1-yl, azonan-1-yl, morpholin-4-yl, tetrahydroisoquinolin-2-yl or 3,5-dimethyl-pyrazol-1-yl radical, or a piperazin-1-yl radical substituted in 4-position by R19, in which
if R7 is a radical of the formula (d),
R16 is hydrogen, and
R17 and R18, together and with inclusion of the N—C(—)—N structure to which they are bonded are Aryl2,
Aryl1 is benzimidazol-2-yl, 5-nitrobenzimidazol-2-yl, 5-chlorobenzimidazol-2-yl or 5-methylbenzimidazol-2-yl,
Aryl2 is imidazol-2-yl, 4-methyl-imidazol-2-yl, 4-ethyl-benzimidazol-2-yl, 4-acetyl-imidazol-2-yl, 1H-[1,2,4]triazol-3-yl, benzimidazol-2-yl, 1-methyl-benzimidazol-2-yl, 1-ethyl-benzimidazol-2-yl, 5,6-dimethyl-benzimidazol-2-yl, purin-8-yl, 1,6-dimethylimidazo[4,5-b]pyridin-2-yl or 1,5,6-trimethylimidazo[4,5-b]pyridin-2-yl,
R19 is 1-4C-alkyl or 1-4C-alkylcarbonyl,
R20 is halogen, nitro, 1-4C-alkyl or 1-4C-alkoxy, the salts of these compounds, as well as the N-oxides, enantiomers, E/Z isomers and tautomers of these compounds and their salts.

Preferred compounds of the formula 1 are those in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy, R3 is hydrogen,
R31 is hydrogen,
either, in a first embodiment (embodiment a) according to the present invention,
R4 is —O—R41, in which
R41 is hydrogen or 1-4C-alkylcarbonyl, and
R5 is hydrogen,
or, in a second embodiment (embodiment b) according to the present invention,
R4 is hydrogen, and
R5 is —O—R51, in which
R51 is hydrogen or 1-4C-alkylcarbonyl,
R6 is hydrogen,
R7 is a radical selected from

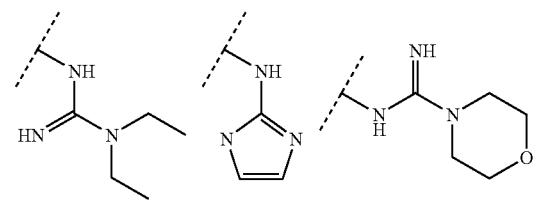

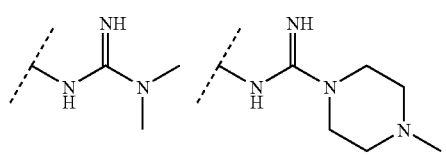

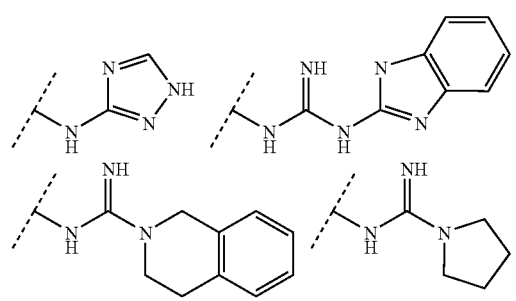

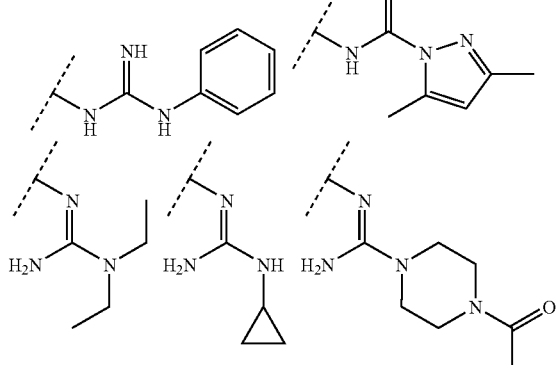

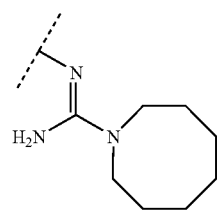

the salts of these compounds, as well as the N-oxides, enantiomers, E/Z isomers and tautomers of these compounds and their salts.

More preferred compounds of the formula 1 are those in which

R1 is 1-2C-alkoxy, or completely or predominantly fluorine-substituted 1-2C-alkoxy, R2 is 1-2C-alkoxy, or predominantly fluorine-substituted 1-2C-alkoxy, R3 is hydrogen, R31 is hydrogen, R4 is —O—R41, in which R41 is hydrogen or 1-4C-alkylcarbonyl, and R5 is hydrogen, R6 is hydrogen, R7 is a radical of formula (c)

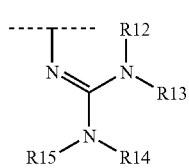

(c)

in which either

R12 is hydrogen,

R13 is hydrogen,

R14 is hydrogen or 1-4C-alkyl, and

R15 is 1-4C-alkyl or 3-7C-cycloalkyl, or

R12 is hydrogen,

R13 is hydrogen, and

R14 and R15, together and including the nitrogen atom to which both are bonded, are a pyrrolidin-1-yl, piperidin-1-yl, azepan-1-yl, azocan-1-yl, azonan-1-yl or morpholin-4-yl, radical, or a piperazin-1-yl radical substituted in 4-position by R19, in which R19 is 1-4C-alkylcarbonyl, the salts of these compounds, as well as the N-oxides, enantiomers, E/Z isomers and tautomers of these compounds and their salts.

Yet more preferred compounds of the formula 1 are those in which

R1 is methoxy, or ethoxy,

R2 is methoxy, ethoxy, 2,2-difluoroethoxy, or difluoromethoxy,

R3 is hydrogen,

R31 is hydrogen,

R4 is —O—R41, in which

R41 is hydrogen, and

R5 is hydrogen,

R6 is hydrogen,

R7 is bonded to the meta or para position with respect to the binding position in which the phenyl ring is bonded to the phenanthridine ring system, and is a radical of formula (c)

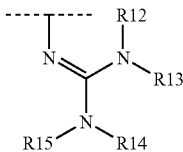

(c)

in which
either
R12 is hydrogen,
R13 is hydrogen,
R14 is 1-4C-alkyl, such as e.g. 1-2C-alkyl, and
R15 is 1-4C-alkyl, such as e.g. 1-2C-alkyl,
or
R12 is hydrogen,
R13 is hydrogen,
R14 is hydrogen, and
R15 is 3-5C-cycloalkyl, such as e.g. cyclopropyl,
or
R12 is hydrogen,
R13 is hydrogen, and
R14 and R15, together and including the nitrogen atom to which both are bonded, are a pyrrolidin-1-yl, piperidin-1-yl, azepan-1-yl, azocan-1-yl, azonan-1-yl or morpholin-4-yl radical, or a piperazin-1-yl radical substituted in 4-position by R19, in which
R19 is 1-4C-alkylcarbonyl, the salts of these compounds, as well as the N-oxides, enantiomers, E/Z isomers and tautomers of these compounds and their salts.

In particular preferred compounds of the formula 1 are those in which
R1 is methoxy,
R2 is methoxy, ethoxy, difluoromethoxy, or 2,2-difluoroethoxy,
R3 is hydrogen,
R31 is hydrogen,
R4 is —O—R41, in which
R41 is hydrogen, and
R5 is hydrogen,
R6 is hydrogen,
R7 is bonded to the meta or para position with respect to the binding position in which the phenyl ring is bonded to the phenanthridine ring system, and is a radical of formula (c)

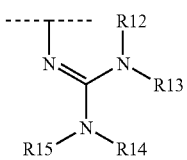

(c)

in which
either
R12 is hydrogen,
R13 is hydrogen,
R14 is ethyl, and
R15 is ethyl, or
R12 is hydrogen,
R13 is hydrogen,
R14 is hydrogen, and
R15 is cyclopropyl,
or
R12 is hydrogen,
R13 is hydrogen, and
R14 and R15, together and including the nitrogen atom to which both are bonded, are an azocan-1-yl radical, or a piperazin-1-yl radical substituted in 4-position by R19, in which
R19 is acetyl, the salts of these compounds, as well as the N-oxides, enantiomers, E/Z isomers and tautomers of these compounds and their salts.

A special interest in the compounds according to this invention relates to those compounds which are included—within the scope of this invention—by one or, when possible, by more of the following embodiments:

A special embodiment of the compounds of the present invention include those compounds of formula 1 in which R1 and R2 are independently 1-2C-alkoxy, 2,2-difluoroethoxy, or completely or predominantly fluorine-substituted 1-2C-alkoxy.

Another special embodiment of the compounds of the present invention include those compounds of formula 1 in which R1 and R2 are independently 1-2C-alkoxy, 2,2-difluoroethoxy, or completely or predominantly fluorine-substituted 1-2C-alkoxy, and R3 and R31 are both hydrogen.

Another special embodiment of the compounds of the present invention include those compounds of formula 1 in which R1 and R2 are independently 1-2C-alkoxy, 2,2-difluoroethoxy, or completely or predominantly fluorine-substituted 1-2C-alkoxy, and R3, R31 and R6 are all hydrogen.

Another special embodiment of the compounds of the present invention include those compounds of formula 1 in which R1 and R2 are independently 1-2C-alkoxy, 2,2-difluoroethoxy, or completely or predominantly fluorine-substituted 1-2C-alkoxy, R3, R31 and R6 are hydrogen, and R7 is a radical of formula (c).

Another special embodiment of the compounds of the present invention include those compounds of formula I in which one of R1 and R2 is methoxy, and the other is methoxy, ethoxy, difluoromethoxy or 2,2-difluoroethoxy, and R3 and R31 are both hydrogen.

Another special embodiment of the compounds of the present invention include those compounds of formula I in which R1 is ethoxy or, particularly, methoxy, and R2 is methoxy, or, particularly, ethoxy, difluoromethoxy or 2,2-difluoroethoxy, and R3 and R31 are both hydrogen.

Another special embodiment of the compounds of the present invention include those compounds of formula I in which R1 is methoxy, and R2 is 2,2-difluoroethoxy, and R3 and R31 are both hydrogen.

Another special embodiment of the compounds of the present invention include those compounds of formula I in which R1 is methoxy, and R2 is ethoxy, and R3 and R31 are both hydrogen.

Another special embodiment of the compounds of the present invention include those compounds of formula I in which R1 is methoxy, and R2 is difluoromethoxy, and R3 and R31 are both hydrogen.

Another special embodiment of the compounds of the present invention include those compounds of formula I in which R6 is hydrogen.

Another special embodiment of the compounds of the present invention include those compounds of formula I, in which R5 or, particularly, R4 is the radical (1-4C-alkylcarbonyl)-O— such as e.g. acetoxy, or hydroxyl, and all the other substituents are as defined in any compound of the present invention as defined above.

Another special embodiment of the compounds of the present invention include those compounds of the formula 1 in which R5 or, particularly, R4 is hydroxyl.

A preferred embodiment according to the present invention is embodiment a.

A further preferred embodiment of the compounds of the present invention include compounds according to embodiment a, in which R5 and R41 are both hydrogen, and in which R1 and R2 are independently 1-2C-alkoxy, 2,2-difluoroethoxy, or completely or predominantly fluorine-substituted 1-2C-alkoxy, and R3, R31 and R6 are all hydrogen.

A yet further preferred embodiment of the compounds of the present invention include compounds according to embodiment a, in which R5 is hydrogen, and in which R1 is methoxy, and R2 is ethoxy, difluoromethoxy or 2,2-difluoroethoxy, and R3, R31 and R6 are all hydrogen.

A still yet further preferred embodiment of the compounds of the present invention include compounds according to embodiment a, in which R5 and R41 are both hydrogen, and in which R1 is methoxy, and R2 is ethoxy, difluoromethoxy or 2,2-difluoroethoxy, and R3, R31 and R6 are all hydrogen.

Suitable compounds according to the present invention more worthy to be mentioned include those compounds of formula 1, in which R5 or, particularly, R4 is hydroxyl.

Exemplary compounds according to the present invention may include those selected from
1. N'-(1-{4-[(2RS,4aRS,10bRS)-9-(1,1-Difluoro-methoxy)-2-hydroxy-8-methoxy-1,2,3,4,4a,10b-hexahydro-phenanthridin-6-yl]-phenyl}-methanoyl)-N,N-diethyl-guanidine
2. N-(1-Amino-1-azocan-1-yl-methylene)-4-[(2RS,4aRS,10bRS)-9-(1,1-difluoro-methoxy)-2-hydroxy-8-methoxy-1,2,3,4,4a,10b-hexahydro-phenanthridin-6-yl]-benzamide
3. N-Cyclopropyl-N'-(1-{4-[(2RS,4aRS,10bRS)-9-(1,1-difluoro-methoxy)-2-hydroxy-8-methoxy-1,2,3,4,4a,10b-hexahydro-phenanthridin-6-yl]-phenyl}-methanoyl)-guanidine
4. N-[1-(4-Acetyl-piperazin-1-yl)-1-amino-methylene]-4-((2RS,4aRS,10bRS)-2-hydroxy-8,9-dimethoxy-1,2,3,4,4a,10b-hexahydro-phenanthridin-6-yl)-benzamide
5. N,N-Diethyl-N'-{1-[4-((2RS,4aRS,10bRS)-2-hydroxy-8,9-dimethoxy-1,2,3,4,4a,10b-hexahydro-phenanthridin-6-yl)-phenyl]-methanoyl}-guanidine and
6. N-(1-Amino-1-azocan-1-yl-methylene)-4-((2RS,4aRS,10bRS)-2-hydroxy-8,9-dimethoxy-1,2,3,4,4a,10b-hexahydro-phenanthridin-6-yl)-benzamide, the salts of these compounds, as well as the N-oxides, enantiomers, E/Z isomers and tautomers of these compounds and their salts.

Preferably, the compounds according to the present invention which are listed in the Table A in the appended "Biological Investigations" as well as their salts, are to be mentioned as a particular interesting aspect of the present invention.

The compounds of formula 1 are chiral compounds having chiral centers at least in positions 4a and 10b and depending on the meanings of R3, R31, R4 and R5 additional chiral centers in positions 1, 2, 3 and 4.

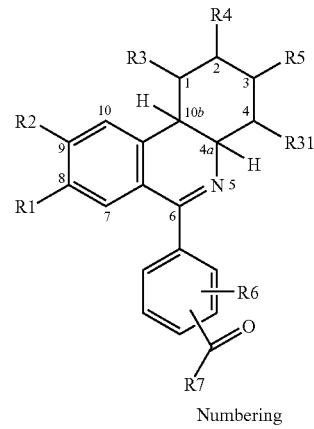

Numbering

The invention includes all conceivable stereoisomers in pure form as well as in any mixing ratio. Preference is given to compounds of formula 1 in which the hydrogen atoms in positions 4a and 10b are in the cis position relative to one another. The pure cis enantiomers and their mixtures in any mixing ratio and including the racemates are more preferred in this context.

Particularly preferred in this context are those compounds of formula 1, which have with respect to the positions 4a and 10b the configuration shown in formula (1*):

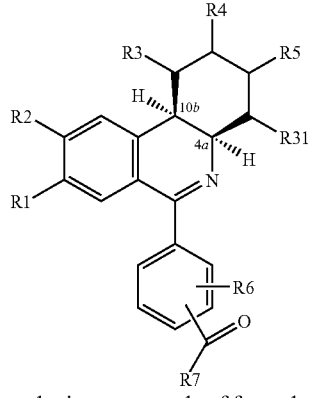

If, for example, in compounds of formula 1* R3, R31 and R5 have the meaning hydrogen and R4 has the meaning —OR41, then the configuration—according to the rules of Cahn, Ingold and Prelog—is R in the 4a position and R in the 10b position.

Preferred compounds of the formula 1 according to embodiment a are those which have, with respect to the positions 2, 4a and 10b, the same configuration as shown in the formulae 1a and 1a* and 1a****:

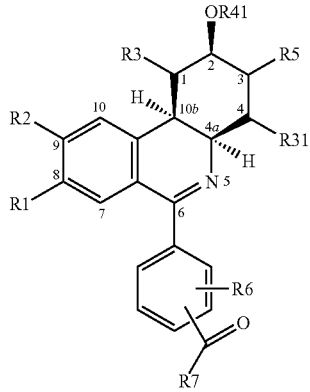

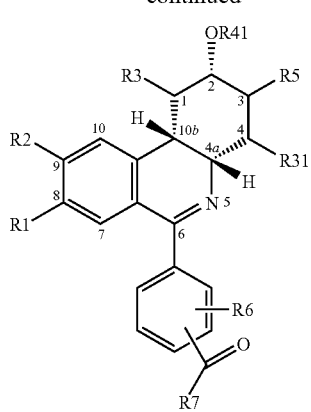

(1a***)

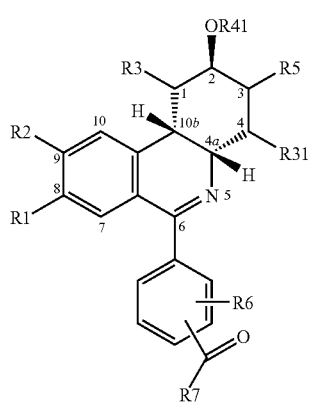

(1a****)

If, for example in compounds of the formula 1a** R3, R31 and R5 have the meaning hydrogen, then the configuration—according to the rules of Cahn, Ingold and Prelog—is S in the position 2, R in the position 4a and R in the position 10b.

If, for example in compounds of the formula 1a*** R3, R31 and R5 have the meaning hydrogen, then the configuration—according the rules of Cahn, Ingold and Prelog—is R in the position 2, S in the position 4a and S in the position 10b.

If, for example in compounds of the formula 1a**** R3, R31 and R5 have the meaning hydrogen, then the configuration—according the rules of Cahn, Ingold and Prelog—is S in the position 2, S in the position 4a and S in the position 10b.

In more particular preferred compounds of the formula 1 according to embodiment a are those which have, with respect to the positions 2, 4a and 10b, the same configuration as shown in the formula 1a*****:

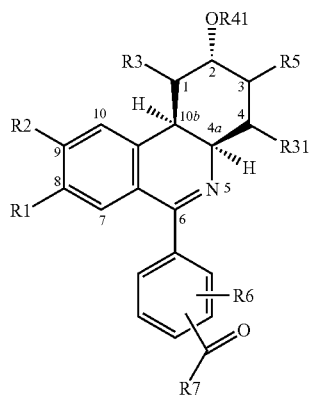

(1a*****)

If, for example in compounds of the formula 1a***** R3, R31 and R5 have the meaning hydrogen, then the configuration—according the rules of Cahn, Ingold and Prelog—is R in the position 2, R in the position 4a and R in the position 10b.

Preferred compounds of the formula 1 according to embodiment b are those which have, with respect to the positions 3, 4a and 10b, the same configuration as shown in the formulae 1b and 1b* and 1b****:

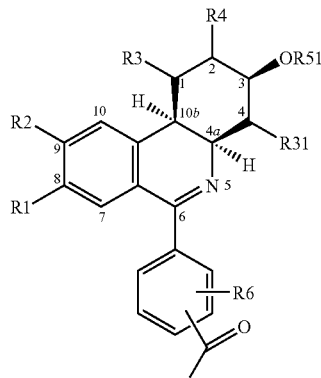

(1b**)

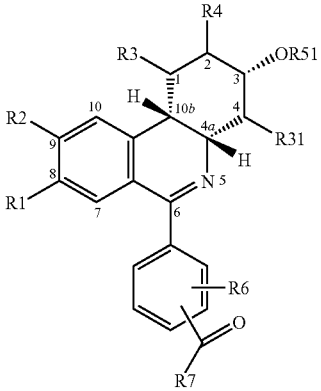

(1b***)

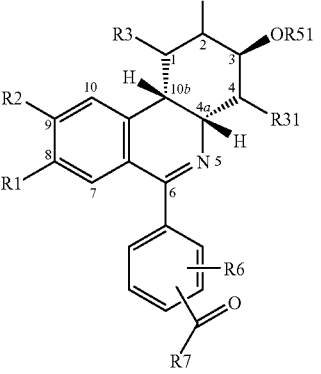

(1b****)

If, for example in compounds of the formula 1b** R3, R31 and R4 have the meaning hydrogen, then the configuration—according the rules of Cahn, Ingold and Prelog—is R in the position 3, R in the position 4a and R in the position 10b.

If, for example in compounds of the formula 1b*** R3, R31 and R4 have the meaning hydrogen, then the configuration—according the rules of Cahn, Ingold and Prelog—is S in the position 3, S in the position 4a and S in the position 10b.

If, for example in compounds of the formula 1b**** R3, R31 and R4 have the meaning hydrogen, then the configuration—according the rules of Cahn, Ingold and Prelog—is R in the position 3, S in the position 4a and S in the position 10b.

More preferred compounds of the formula 1 according to embodiment b are those which have, with respect to the positions 3, 4a and 10b, the same configuration as shown in the formula 1b*****:

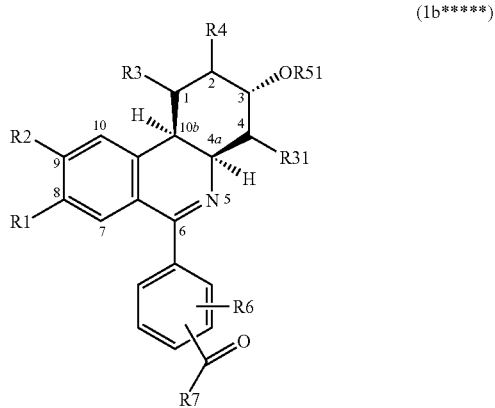

(1b*****)

If, for example in compounds of the formula 1b***** R3, R31 and R4 have the meaning hydrogen, then the configuration—according the rules of Cahn, Ingold and Prelog—is S in the position 3, R in the position 4a and R in the position 10b.

Within the meaning of the embodiments a and b according to this invention, compounds of formula 1a***** are in particular to be emphasized.

The enantiomers can be separated in a manner known per se (for example by preparation and separation of appropriate diastereoisomeric compounds). Thus, e.g. an enantiomer separation can be carried out at the stage of the starting compounds having a free amino group such as starting compounds of formulae 7 or 9b as defined below.

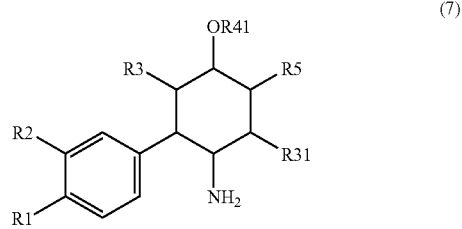

(7)

Separation of the enantiomers can be carried out, for example, by means of salt formation of the racemic compounds of the formulae 7 or 9b with optically active acids, preferably carboxylic acids, subsequent resolution of the salts and release of the desired compound from the salt. Examples of optically active carboxylic acids which may be mentioned in this connection are the enantiomeric forms of mandelic acid, tartaric acid, O,O'-dibenzoyltartaric acid, camphoric acid, quinic acid, glutamic acid, pyroglutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formulae 7 or 9b can be prepared via asymmetric syntheses. Enantiomerically pure starting compounds as well as enantiomerically pure compounds of the formula 1 can be also obtained by chromatographic separation on chiral separating columns; by derivatization with chiral auxiliary reagents, subsequent diastereomer separation and removal of the chiral auxiliary group; or by (fractional) crystallization from a suitable solvent.

The compounds according to the invention can be prepared, for example, as shown in the reaction schemes below and according to the following specified reaction steps, or, particularly, in a manner as described by way of example in the following examples, or analogously or similarly thereto using preparation procedures known to the person skilled in the art.

Reaction scheme 1 shows the preparation of compounds of formula 1.

Starting with the compounds of formula 4, in which R1, R2, R3, R31, R4, R5 and R6 have the meanings mentioned above and C(O)OR stands for a suitable ester group such as an alkyl ester (preferably a methyl ester group), the compounds of formula 1, in which R1, R2, R3, R31, R4, R5, R6 and R7 have the abovementioned meanings, can be obtained by different routes. On the one hand, the compounds of formula 1 may be obtained from the compounds of formula 4 by direct reaction with compounds of formula R7-H, in which R7 has the meanings given above.

On the other hand the compounds of formula 4 can be first saponified to give the benzoic acid derivatives of formula 3

Compounds of formula 3, in which R1, R2, R3, R31 and R6 have the meanings mentioned above and R4 or R5 is hydroxyl, (obtainable, for example, from corresponding compounds of formula 4, in which R4 or R5 is acyloxy, by the abovementioned saponification step affording, beside the free benzoic acid group, the respective desacylated free hydroxyl group) should be protected by a suitable temporary protective group or, preferably, via acylation, such as e.g. via acetylation, reaction known per se to the skilled person or as described in the following examples, using e.g. the acid chlorides, before further reaction.

Benzoic acid derivatives of formula 3 can then be activated prior to the reaction with compounds of formula R7-H for example by forming an acid halide or acid anhydride, or by using coupling agents known to the person skilled in the art, such as, for example, N,N'-dicyclohexylcarbodiimide, N'-(3-dimethylaminopropyl)-N-ethylcarbodiimide hydrochloride (EDCI) or 2-(1H-benzotriazole-1-yl)-1,1,3,3-tetramethyluronium hexafluorophosphate (HBTU) (compounds of formula 2).

Reaction scheme 1:

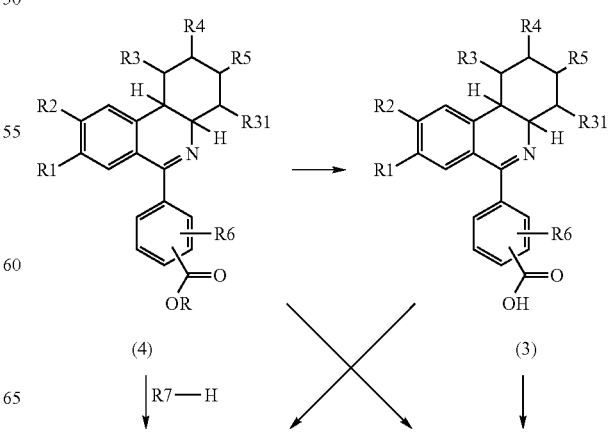

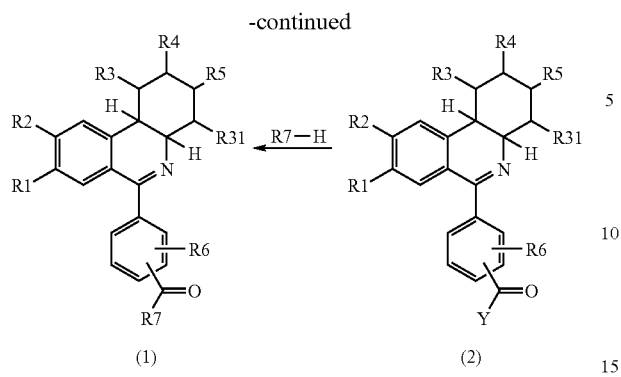

(1)       (2)

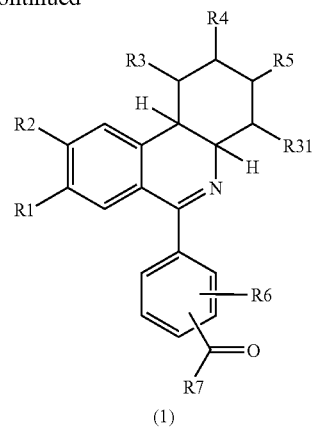

(1)

As shown in reaction scheme 2, it is also possible to obtain compounds of formula 1 from compounds of formula 3 or from compounds of formula 2 by initially reacting the compounds of formula 3 under suitable coupling conditions (using appropriate coupling agents and additives) or, respectively, compounds of formula 2, in which Y is for example a chlorine atom, with suitably substituted S-alkyl-isothioureas and then, in a second step, replacing the S-alkyl group by a suitably substituted amine.

Similarly as stated above, the hydroxyl group in the position 2 or 3 of the compounds of formula 3 or 2 should suitably be protected by an appropriate temporary or permanent protecting group, preferably, an acyl group (such as e.g. acetyl) prior to said reaction.

Reaction scheme 2:

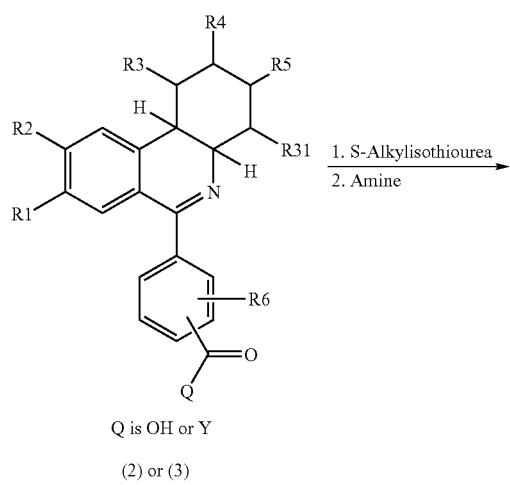

Q is OH or Y (2) or (3)

Similar reactions are described, for example in Arzneim.-Forsch. (Drug Res.) 25, No. 10, (1975), pp. 1477-1482 or in the following examples.

Optionally, compounds of formula 1 can be converted into further compounds of the formula 1 by methods known to one of ordinary skill in the art. More specifically, for example, from compounds of the formula 1 in which a) R4 or R5 is hydroxyl, the corresponding ester compounds can be obtained by esterification reactions;
b) R4 or R5 is hydroxyl, the corresponding ether compounds can be obtained by etherification reactions;
c) R4 or R5 is an acyloxy group, such as e.g. acetyl, the corresponding hydroxyl compounds can be obtained by deesterification, e.g. saponification, reactions;

The methods mentioned under a), b) and c) are expediently carried out analogously to the methods known to the person skilled in the art or as described by way of example in the following examples.

Optionally, compounds of the formula 1 can be converted into their salts, or, optionally, salts of the compounds of the formula 1 can be converted into the free compounds.

In addition, the compounds of the formula 1 can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

Compounds of formula 4 according to embodiment a can be prepared as described and shown in reaction scheme 3 below.

In the first reaction step of the synthesis route shown in scheme 3, compounds of the formula 8, in which R1, R2, R3, R31, R41 and R5 have the meanings mentioned above in embodiment a and R41 is other than hydrogen, are prepared from the corresponding compounds of the formula 9 by introduction of the group R41. The introduction reaction is carried out in a manner habitual per se or as described by way of example in the following examples.

Reaction scheme 3:

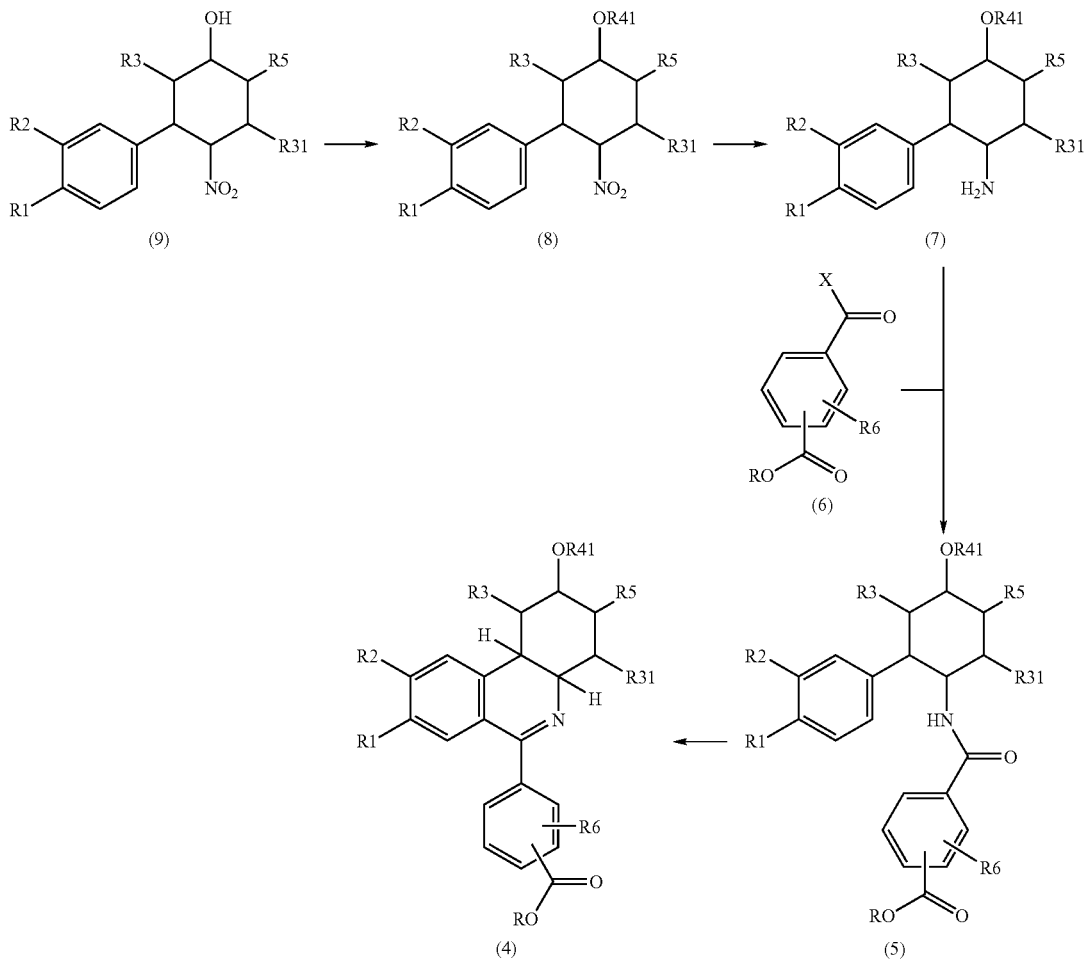

In the next reaction step of synthesis route, the nitro group of compounds of the formula 8, in which R1, R2, R3, R31, R41 and R5 have the meanings mentioned above in embodiment a and R41 is other than hydrogen, is reduced to the amino group of the corresponding compounds of the formula 7. Said reduction is carried out in a manner known to the person skilled in the art, for example as described in J. Org. Chem. 1962, 27, 4426 or as described in the following examples. In more detail, the reduction can be carried out, for example, by catalytic hydrogenation, e.g. in the presence of Raney nickel or a noble metal catalyst such as palladium on active carbon, in a suitable solvent such as methanol or ethanol at room temperature and under normal or elevated pressure. Optionally, a catalytic amount of an acid, such as, for example, hydrochloric acid, can be added to the solvent. Preferably, however, the reduction is carried out using a hydrogen-producing mixture, for example, metals such as zinc, zinc-copper couple or iron with organic acids such as acetic acid or mineral acids such as hydrochloric acid. More preferably, the reduction is carried out using a zinc-copper couple in the presence of an organic or an inorganic acid. Such a zinc-copper couple is accessible in a way known to the person of ordinary skill in the art.

Compounds of the formula 5, in which R1, R2, R3, R31, R41, R5 and R6 have the meanings indicated above in embodiment a, R41 is other than hydrogen and C(O)OR stands for a suitable ester group, preferably the methyl ester group, are accessible from the corresponding compounds of the formula 7, by reaction with corresponding compounds of the formula 6, in which X represents a suitable leaving group, preferably a chlorine atom.

Alternatively, compounds of the formula 5 can also be prepared from the corresponding compounds of the formula 7 and corresponding compounds of the formula 6, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Compounds of the formula 6 are either known or can be prepared in a known manner.

Compounds of the formula 4, in which R1, R2, R3, R31, R41, R5 and R6 have the meanings as given in embodiment a, R41 is other than hydrogen and C(O)OR stands for a suitable ester group, preferably the methyl ester group, can be obtained by cyclocondensation of corresponding compounds of the formula 5.

Said cyclocondensation reaction is carried out in a manner known per se to the person skilled in the art or as described by way of example in the following examples, according to Bischler-Napieralski (e.g. as described in J. Chem. Soc., 1956, 4280-4282) in the presence of a suitable condensing agent, such as, for example, polyphosphoric acid, phosphorus pentachloride, phosphorus pentoxide or phosphorus oxychloride, in a suitable inert solvent, e.g. in a chlorinated hydrocarbon such as chloroform, or in a cyclic hydrocarbon such as toluene or xylene, or another inert solvent such as isopropyl acetate or acetonitrile, or without further solvent using an excess of condensing agent, at reduced temperature, or at room temperature, or at elevated temperature or at the boiling temperature of the solvent or condensing agent used.

Below reaction scheme 4 shows the synthesis of compounds of the formula 9, in which R1, R2, R3, R31 and R5 have the meanings indicated above in embodiment a, from corresponding compounds of the formula 10 via reduction reaction of the carbonyl group. Suitable reducing agents for the abovementioned reduction reaction may include, for example, metal hydride compounds such as, for example, diisopropylaluminium hydride, borane, sodium borohydride, sodium triacetoxyborohydride, sodium cyanoborohydride, zinc borohydride, potassium tri-sec-butylborohydride, sodium tri-sec-butylborohydride, lithium tri-sec-butylborohydride, β-isopinocampheyl-9-borabicyclo[3.3.1]nonane and the like. The preferred examples of said reducing agents are sodium cyanoborohydride, β-isopinocampheyl-9-borabicyclo[3.3.1]nonane and potassium tri-sec-butylborohydride. The most preferred examples of the abovementioned reducing agents are β-isopinocampheyl-9-borabicyclo[3.3.1]nonane and potassium tri-sec-butylborohydride, which both allow to prepare compounds of the formula 10 stereoselectively. "Stereoselectively" in this connection means that those compounds of the formula 10, in which the hydrogen atoms in positions 1 and 3 are located at the opposite side of the plane defined by the cyclohexane ring, are obtained preferentially.

Reaction scheme 4:

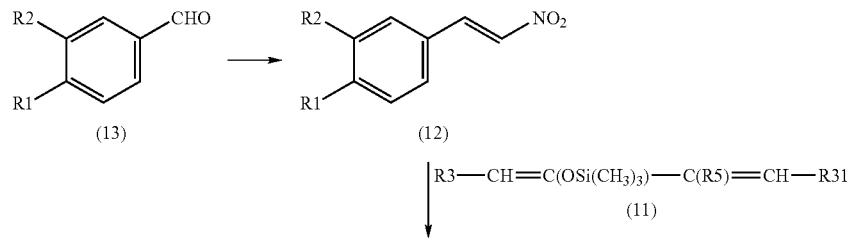

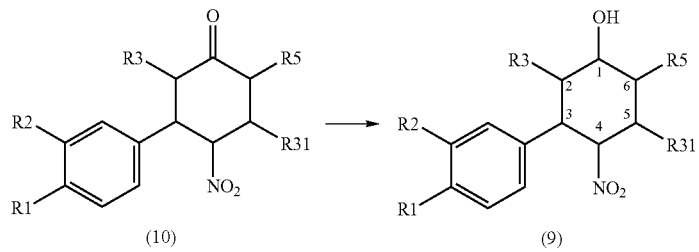

The compounds of the formula 10, in which R1, R2, R3, R31 and R5 have the meanings mentioned in embodiment a, are either known or can be obtained by the reaction of compounds of the formula 12, in which R1 and R2 have the meanings mentioned above in embodiment a, with compounds of the formula 11, in which R3, R31 and R5 have the meanings mentioned above in embodiment a. The cycloaddition reaction is carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formulae 8 or 9, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae 11 and 12 are either known or can be prepared in a known manner. The compounds of the formula 12 can be prepared, for example, in a manner known to the person skilled in the art from corresponding compounds of the formula 13 as described, for example, in J. Chem. Soc. 1951, 2524 or in J. Org. Chem. 1944, 9, 170 or as described in the following examples.

The compounds of the formula 13, in which R1 and R2 have the meanings indicated above, are either known or can be prepared in a manner known to the person skilled in the art, as described, for example, in Ber. Dtsch. Chem. Ges. 1925, 58, 203.

Compounds of formula 4 according to embodiment b can be prepared as described and shown in reaction scheme 5 below.

In the first reaction step in reaction scheme 5 below, the nitro group of compounds of the formula 10b, in which R1, R2, R3, R31 and R4 have the meanings indicated in embodiment b above, is reduced to obtain corresponding compounds of the formula 9b. Said reduction reaction is carried out in a manner known to the person skilled in the art, for example as described in J. Org. Chem. 1962, 27, 4426 or as described in the following examples. More specifically, the reduction can be carried out, for example, by contacting compounds of the formula 10b with a hydrogen-producing mixture such as, preferably, metallic zinc in a mildly acidic medium such as acetic acid in a lower alcohol such as methanol or ethanol at room temperature or at elevated temperature or, preferably, at the boiling temperature of the solvent mixture. Alternatively, the reduction can be carried out by selective reduction of the nitro group in a manner known to the person skilled in the art, for example by hydrogen transfer reaction in the presence of a metal catalyst, for example palladium or preferably Raney nickel, in a suitable solvent, preferably a lower alcohol, using, for example ammonium formiate or preferably hydrazine hydrate as hydrogen donor.

Compounds of the formula 9b obtained can be reacted, for example, as described by way of example in the following examples with compounds of the formula 6, in which R6 has the meanings given above, C(O)OR stands for a suitable ester group, preferably the methyl ester group, and X represents a suitable leaving group, preferably a chlorine atom, to give corresponding compounds of the formula 8b.

Alternatively, compounds of the formula 8b, in which R1, R2, R3, R31, R4 and R6 have the meanings given above in embodiment b and C(O)OR stands for said suitable ester group, can also be prepared, for example, from corresponding compounds of the formula 9b and corresponding compounds of the formula 6, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Reaction scheme 5:

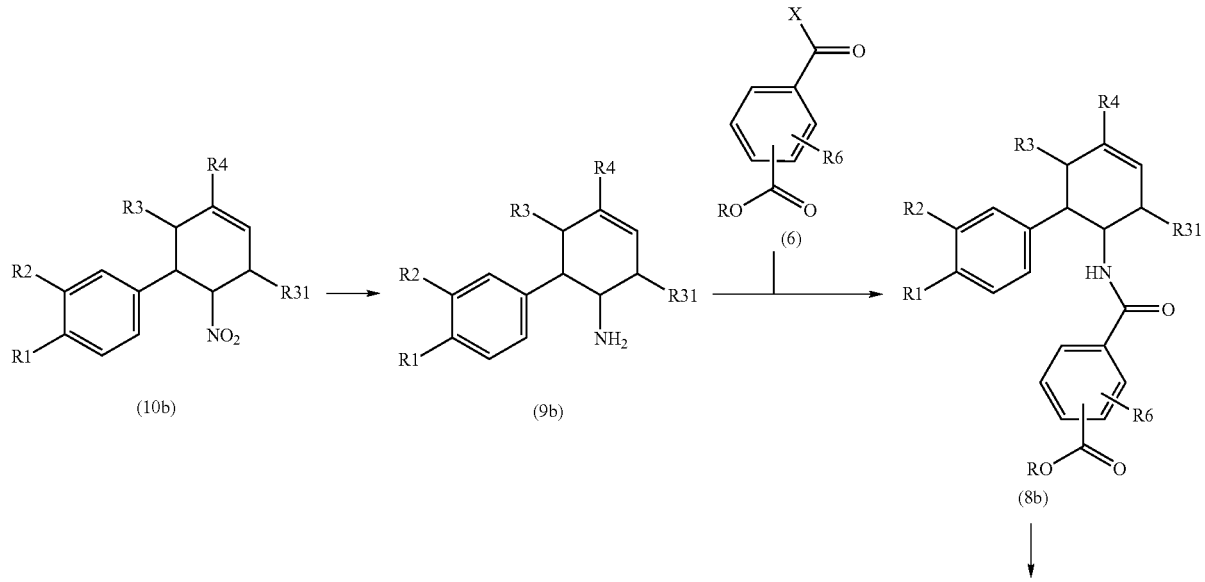

-continued

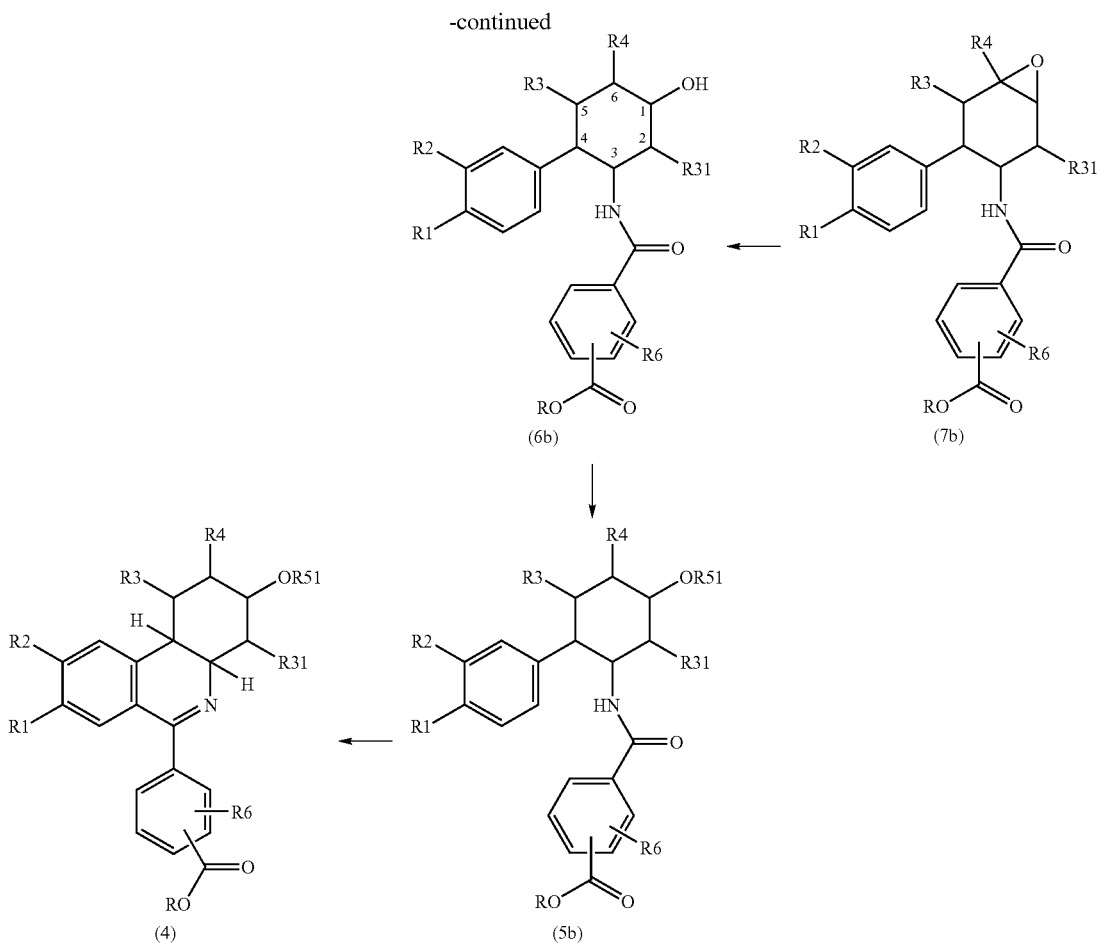

In the next step compounds of the formula 8b can be converted into corresponding compounds of the formula 7b by epoxidation reaction, which can be carried out as described in the following examples or in a manner known to one of ordinary skill in the art employing, for example, suitable epoxidation methods or suitable epoxidation reagents such as, for example, peracids (e.g. m-chloroperbenzoic acid) or organic or inorganic peroxides (e.g. dimethyldioxirane, hydrogene peroxide or persulfates).

Compounds of the formula 7b obtained can be reduced by art-known methods to corresponding compounds of the formula 6b. More specifically, said reduction reaction can be performed employing, for example, as described by way of example in the following examples sodium borohydride as reductant. Alternatively, said reduction reaction can be also carried out using, for example, lithium aluminium hydride or a reductive mixture comprising noble metals, such as platinium dioxide or palladium, and a suitable hydrogen donor. With the aid of each of those said reduction methods, compounds of the formula 7b can be converted largely regio- and diastereoselectively into compounds of the formula 6b, wherein the hydroxyl radical in position 1 and the amido radical in position 3 are located at the same side of the plane defined by the cyclohexane ring.

It is moreover known to one of ordinary skill of the art, that the absolute configuration of a chiral carbon atom, preferably, to which a hydroxyl group and a hydrogen atom are bonded, can be inverted. Thus the configuration of the carbon atom in position 1 of compounds of the formula 6b can be optionally inverted. Said inversion of configuration of position 1 of compounds of the formula 6b can be achieved in a manner familiar to the person skilled in the art, for example by derivatization of position 1 with a suitable leaving group and subsequent replacement of said leaving group by a suitable nucleophile in a nucleophilic substitution reaction according to SN2 mechanism. Alternatively, said inversion of configuration of position 1 of compounds of the formula 6b can be also obtained, for example, as described by way of example in the following examples according to subsequently specified two step procedure shown in reaction scheme 6 below. In more detail, in the first step of said procedure shown in reaction scheme 6, exemplary compounds of the formula 6b*, in which R1, R2, R6 have the meanings indicated above, C(O)OR stands for said suitable ester group (preferably the methyl ester group) and R3, R31, R4 are hydrogen and position 1 has the R configuration, are converted by oxidation reaction into corresponding compounds of the formula 11b. Said oxidation is likewise carried out under conditions customary per se using, for example, chloranil, atmospheric oxygen, manganese dioxide or, preferably, chromium oxides as an oxidant. Then in the second step, compounds of the formula 11b obtained are converted by art-known reduction reaction of the keto group, preferably with metal hydride compounds or, more specifically, metal borohydrides, such as, for example, sodium borohydride, into corresponding compounds of formula 6b**, in which position 1 has now S configuration and thus the configuration of the carbon atom in position 1 is now inverted regarding to said compounds of the formula 6b*.

Reaction scheme 6:

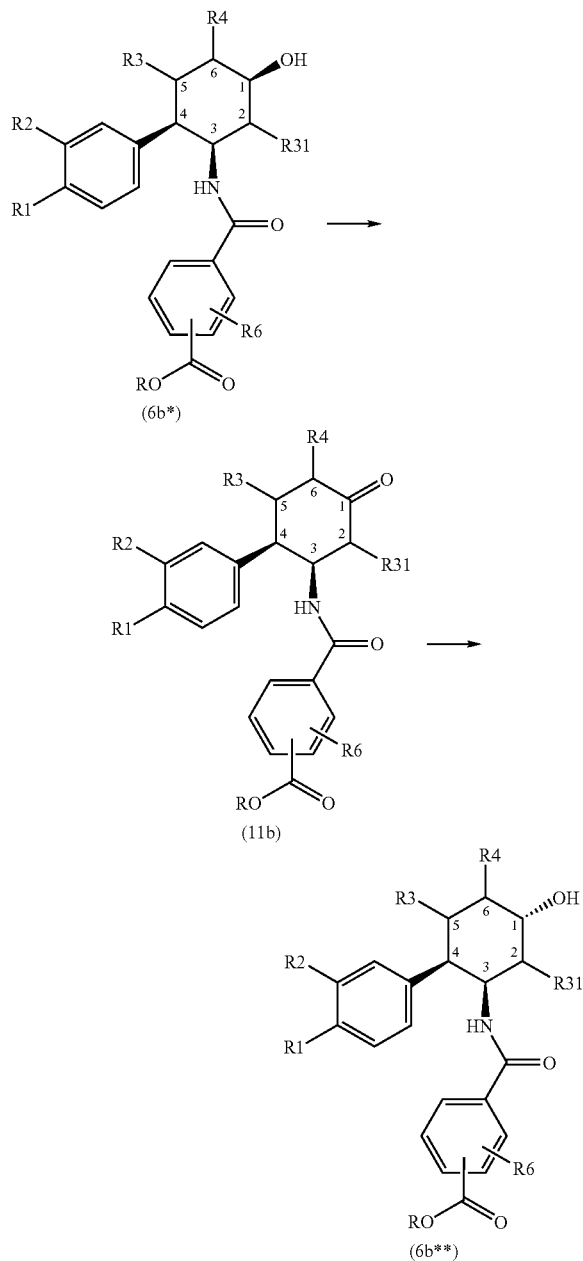

In the next reaction step of the synthesis route shown in reaction scheme 5 shown above, compounds of the formula 6b are converted into corresponding compounds of the formula 5b by introduction of the group R51, in which R51 is other than hydrogen. The introduction reaction is carried out in a manner habitual per se (e.g. via alkylation or acylation reaction) or as described by way of example in the following examples.

The cyclization reaction leading to compounds of the formula 4 can be carried out, for example, as described by way of example in the following examples or analogously or similarly thereto, or as mentioned above for compounds according to embodiment a.

Compounds of the formula 10b, in which R1, R2, R3, R31 and R4 have the above-mentioned meanings, are either known or can be obtained, for example as shown in reaction scheme 7, by the reaction of compounds of the formula 12, in which R1 and R2 have the abovementioned meanings, with compounds of the formula 12b, in which R3, R31 and R4 have the meanings indicated above.

Reaction scheme 7:

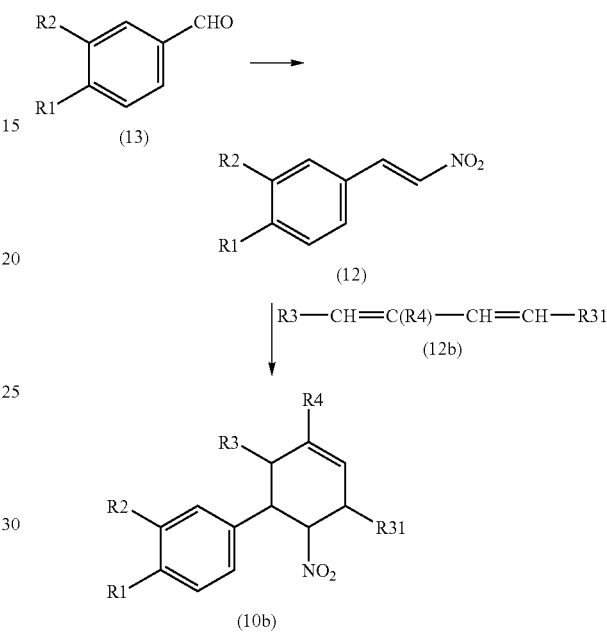

The cycloaddition is in this case carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula 10b, in which the phenyl ring and the nitro group are trans to one another, can be converted such as known to the person skilled in the art into the corresponding cis compounds, e.g. as described in J. Amer. Chem. Soc. 1957, 79, 6559 or as described in the following examples.

The compounds of the formula 12b are either known or can be prepared in a known manner.

In an alternative, compounds of the formula 5b, in which R1, R2, R3, R31, R4, R51 and R6 have the meanings given above in embodiment b whereby R51 is other than hydrogen and C(O)OR stands for said suitable ester group, preferably the methyl ester group, (particularly compounds of formula 5b, in which R1, R2, R51 and R6 have the meanings given above in embodiment b whereby R51 is other than hydrogen, and R3, R31 and R4 are all hydrogen) can also be obtained as shown in reaction scheme 8 and as described by way of example in the following examples.

In the first reaction step of the route outlined in reaction scheme 8, the amino group of compounds of the formula 9b is protected with an art-known protective group PG1, such as e.g. the tertbutoxycarbonyl group. The protected compounds are subjected to hydroboration reaction to obtain over two steps compounds of formula 14b. Said hydroboration reaction is carried out as described in the following examples using an appropriate (hydro)borating agent, such as e.g.

9-BBN, isopinocampheylborane or the like, or, particularly, borane-tetrahydrofuran ($H_3B$-THF), advantageously at ambient temperature. The compounds obtained are then converted into compounds of the formula 14b by introduction of the group R51 whereby R51 is other than hydrogen in a manner analogously as described above.

In the next reaction step of the synthesis route shown in reaction scheme 8, compounds of formula 14b are converted into corresponding compounds of the formula 5b according to embodiment b by deprotection of the protective group PG1 and amidification with compounds of the formula 6. Said reactions are carried out in a manner habitual per se or as described in the specification of this invention or in the following examples.

If necessary, the product obtained via said hydroboration reaction or, suitably, the R51-substituted derivative thereof is purified from resulting stereo- and/or regioisomeric side products by methods known to the person skilled in the art, such as e.g. by chromatographic separation techniques.

Reaction scheme 8:

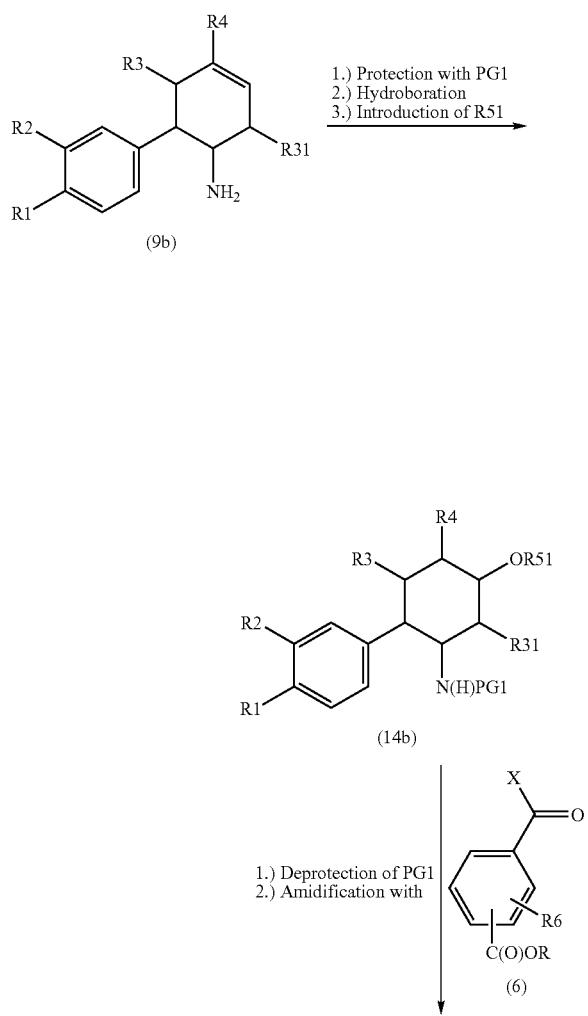

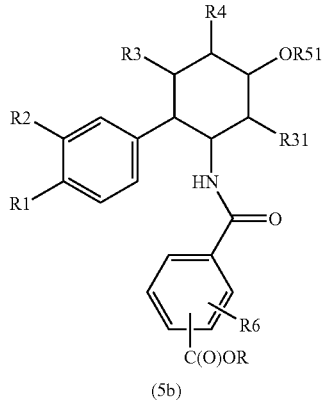

It is also known to the person skilled in the art that, if a plurality of reactive centers are present in a starting material or intermediate, it may be necessary to temporarily block one or more reactive centers with protective groups so that a reaction takes place only at the desired reactive center. A detailed description of how to use a large number of proven protective groups can be found, for example, in T. W. Greene, Protective Groups in Organic Synthesis, John Wiley & Sons, 1991 or 1999 ($3^{rd}$ edition), or in "Protecting Groups (Thieme Foundations Organic Chemistry Series N Group)" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of the formula 1. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims The following examples serve to illustrate the invention further without restricting it. Likewise, further compounds of the formula 1, whose preparation is not explicitly described, can be prepared in an analogous manner or in a manner familiar per se to the person skilled in the art using customary process techniques.

The compounds which are mentioned in the following examples as end products as well as their salts are a preferred subject of the present invention.

In the examples, m.p. stands for melting point, h for hour(s), min for minutes, $R_f$ for retention factor in thin layer chromatography, s.p. for sintering point, EF for empirical formula, MW for molecular weight, MS for mass spectrum, M for molecular ion, other abbreviations have their meanings customary per se to the skilled person. According to common practice in stereochemistry, the symbols RS and SR are used to denote the specific configuration of each of the chiral centers of a racemate. In more detail, for example, the term "(2RS,4aRS,10bRS)" stands for a racemate (racemic mixture) comprising the one enantiomer having the configuration (2R,4aR,10bR) and the other enantiomer having the configuration (2S,4aS,10bS).

EXAMPLES

End Products

1. N'-(1-{4-[(2RS,4aRS,10bRS)-9-(1,1-Difluoro-methoxy)-2-hydroxy-8-methoxy-1,2,3,4,4a,10b-hexahydro-phenanthridin-6-yl]-phenyl}-methanoyl)-N,N-diethyl-guanidine The title compound is obtained in an analogous manner as described for compound 4 using the appropriate starting compound mentioned below as compound 7 to 12.
EF: $C_{27}H_{32}F_2N_4O_4$, MW: 514.58, MS: found: 515.1 ($MH^+$)

2. N-(1-Amino-1-azocan-1-yl-methylene)-4-[(2RS,4aRS,10bRS)-9-(1,1-difluoro-methoxy)-2-hydroxy-8-methoxy-1,2,3,4,4a,10b-hexahydro-phenanthridin-6-yl]-benzamide The title compound is obtained in an analogous manner as described for compound 4 using the appropriate starting compound mentioned below as compound 7 to 12.
EF: $C_{30}H_{36}F_2N_4O_4$, MW: 554.64, MS: found: 555.3 ($MH^+$)

3. N-Cyclopropyl-N'-(1-{4-[(2RS,4aRS,10bRS)-9-(1,1-difluoro-methoxy)-2-hydroxy-4-methoxy-1,2,3,4,4a,10b-hexahydro-phenanthridin-6-yl]-phenyl}-methanoyl)-guanidine The title compound is obtained in an analogous manner as described for compound 4 using the appropriate starting compound mentioned below as compound 7 to 12.
EF: $C_{26}H_{28}F_2N_4O_4$, MW: 498.53, MS: found: 499.2 ($MH^+$)

4. N-[1-(4-Acetyl-piperazin-1-yl)-1-amino-methylene]-4-((2RS,4aRS,10bRS)-2-hydroxy-8,9-dimethoxy-1,2,3,4,4a,10b-hexahydro-phenanthridin-6-yl)-benzamide 484 mg of acetic acid (2RS,4aRS,10bRS)-6-(4-{[1-(4-acetyl-piperazin-1-yl)-1-amino-methylene]-carbamoyl}phenyl)-8,9-dimethoxy-1,2,3,4,4a,10b-hexahydro-phenanthridin-2-yl ester (compound 10) and 137 mg of cesium carbonate are stirred in 10 ml of methanol for 16 h at room temperature. The solvent is removed and the solid residue purified by chromatography on silica gel to yield 235 mg of the title compound.
EF: $C_9H_{35}N_5O_5$, MW: 533.63, MS: found: 534.2 ($MH^+$)

5. N,N-Diethyl-N'-{1-[4-((2RS,4aRS,10bRS)-2-hydroxy-8,9-dimethoxy-1,2,3,4,4a,10b-hexahydro-phenanthridin-6-yl)-phenyl]-methanoyl}guanidine The title compound is obtained in an analogous manner as described for compound 4 using the appropriate starting compound mentioned below as compound 7 to 12.
EF: $C_{27}H_{34}N_4O_4$, MW: 478.6, MS: found 479.1 ($MH^+$)

6. N-(1-Amino-1-azocan-1-yl-methylene)-4-((2RS,4aRS,10bRS)-2-hydroxy-8,9-dimethoxy-1,2,3,4,4a,10b-hexahydro-phenanthridin-6-yl)-benzamide The title compound is obtained in an analogous manner as described for compound 4 using the appropriate starting compound mentioned below as compound 7 to 12.
EF: $C_{30}H_{35}N_4O_4$, MW: 518.66, MS: found: 519.2 ($MH^+$)

The compounds 7 to 9, 11 and 12 are obtained in an analogous manner as described for compound 10 using the appropriate compound A1 or A2 and the appropriate art-known amine compounds.

7. Acetic Acid (2RS,4aRS,10bRS)-6-{4-[1-(N',N'-diethyl-guanidino)-methanoyl]-phenyl}-9-(1,1-difluoro-methoxy)-8-methoxy-1,2,3,4,4a,10b-hexahydro-phenanthridin-2-yl Ester 8. Acetic Acid (2RS,4aRS,10bRS)-6-{4-[(1-amino-1-azocan-1-yl-methylene)-carbamoyl]-phenyl}-9-(1,1-difluoro-methoxy)-8-methoxy-1,2,3,4,4a,10b-hexahydro-phenanthridin-2-yl Ester 9. Acetic Acid (2RS,4aRS,10bRS)-6-{4-[1-(N'-cyclopropyl-guanidino)-methanoyl]-phenyl}-9-(1,1-difluoro-methoxy)-8-methoxy-1,2,3,4,4a,10b-hexahydro-phenanthridin-2-yl Ester 10. Acetic Acid (2RS,4aRS,10bRS)-6-(4-{[1-(4-acetyl-piperazin-1-yl)-1-amino-methylene]-carbamoyl}-phenyl)-8,9-dimethoxy-1,2,3,4,4a,10b-hexahydro-phenanthridin-2-yl Ester 743.4 mg of acetic acid (2RS,4aRS,10bRS)-8,9-dimethoxy-6-{4-[1-(2-methyl-isothioureido)methanoyl]-phenyl}-1,2,3,4,4a,10b-hexahydro-phenanthridin-2-yl ester (compound A1), 384.5 mg of 1-acetylpiperzine and 0.416 ml of triethylamine are stirred in 10 ml of 1,4-dioxane at 90° C. for 5 days. After 2 days another 384.5 mg of 1-acetylpiperazine are added to the reaction mixture. The solvent is removed and the residue three times coevaporated with dichloromethane, than one time with toluene. After redissolving in 25 ml of dichloromethane the solution is extracted with water

41 and aqueous saturated KHCO₃ solution successively and the aqueous KHCO₃ phase reextracted with dichloromethane. After drying the combined organic layers with sodium sulfate the solvent is removed and the residue purified by chromatography on silica to yield 530 mg of the title compound.

11. Acetic Acid (2RS,4aRS,10bRS)-6-{4-[1-(N',N'-diethyl-guanidino)-methanoyl]-phenyl}-8,9-dimethoxy-1,2,3,4,4a,10b-hexahydro-phenanthridin-2-yl Ester 12. Acetic Acid (2RS,4aRS,10bRS)-6-{4-[(1-amino-1-azocan-1-yl-methylene)-carbamoyl]-phenyl}-8,9-dimethoxy-1,2,3,4,4a,10b-hexahydro-phenanthridin-2-yl Ester Starting Compounds A1. Acetic Acid (2RS,4aRS,10bRS)-8,9-dimethoxy-6-{4-[1-(2-methyl-isothioureido)-methanoyl]-phenyl}-1,2,3,4,4a,10b-hexahydro-phenanthridin-2-yl Ester 3.051 g of 4-((2RS,4aRS,10bRS)-2-acetoxy-8,9-dimethoxy-1,2,3,4,4a,10b-hexahydro-phenanthridin-6-yl)-benzoic acid (compound B1), 3.00 g of S-methylisothiourea-sulfate and 10 mg of 4-dimethylaminopyridine are dissolved in 50 ml of acteonitril, than 1.80 g of 1-ethyl-3-(3-dimethylaminopropyl)carbodiimide hydrochloride and 1.23 ml of N-ethyl-diisopropylamin are added. After stirring for 16 hours the solvent is removed. The residue is dissolved in 20 ml of water and extracted with dichloromethane. After drying the combined organic layers with magnesium sulfate the solvent is removed to yield 3.652 g of the title compound as a yellow foam which is directly submitted to further reaction without purification.

A2. Acetic Acid (2RS,4aRS,10bRS)-9-(1,1-difluoro-methoxy)-8-methoxy-6-{4-[1-(2-methyl-isothioureido)-methanoyl]-phenyl}-1,2,3,4,4a,10b-hexahydro-phenanthridin-2-yl Ester The title compound is prepared analogously as described in Example A1 starting from compound B2.

B1. 4-((2RS,4aRS,10bRS)-2-Acetoxy-8,9-dimethoxy-1,2,3,4,4a,10b-hexahydro-phenanthridin-6-yl)-benzoic Acid Hydrochloride 8.1 g of (2RS,4aRS,10bRS)-6-(4-carboxyphenyl)-8,9-dimethoxy-(1,2,3,4,4a,10b)-hexahydro-phenanthridin-2-ol (compound C1) are suspended in 35 ml of dichloromethane and 40 ml of acetyl chloride are added dropwise. After stirring for 1 h at room temperature, the mixture is concentrated and the residue is dissolved in aqueous 1 M disodium hydrogenphosphate solution at pH 67. Under stirring concentrated hydrochloric add is added, the resulting precipitate is filtered off and dried in vacuo to give 4.65 g of the title compound as beige hydrochloride salt.

The free acid is obtained by dissolving the hydrochloride salt in water at pH 6-7, removal of the solvent in vacuo, leaching the resulting yellowish residue with boiling chloroform and concentration of the obtained chloroform solution.

EF: $C_{24}H_{25}NO_6$; MW: 423.47

MS: 424.3 (MH⁺)

42

B2. 4-((2RS,4aRS,10bRS)-2-Acetoxy-9-(1,1-difluoro-methoxy)-8-methoxy-1,2,3,4,4a,10b-hexahydro-phenanthridin-6-yl)-benzoic Acid The title compound is obtained in two steps starting from compound C2 by saponification analogously as described in Example C1 followed by acetylation of obtained intermediate (2RS,4aRS,10bRS)-6-(4-carboxyphenyl)-9-(1,1-difluoro-methoxy)-8-methoxy-(1,2,3,4,4a,10b)-hexahydrophenanthridin-2-ol analogously as described in Example B1.

EF: $C_{24}H_{23}F_2NO_6$; MW: 459.45

MS: 460.3 (MH⁺)

C1. (2RS,4aRS,10bRS)-6-(4-carboxyphenyl)-8,9-dimethoxy-(1,2,3,4,4a,10b)-hexahydrophenanthridin-2-ol A solution of 290 mg of acetic acid (2RS,4aRS,10bRS)-6-(4-methoxycarbonylphenyl)-8,9-dimethoxy(1,2,3,4,4a,10b)-hexahydrophenanthridin-2-yl ester (compound D1) in 10 ml of isopropanol is treated dropwise with aqueous lithium hydroxide solution to adjust to pH 10. Stirring is continued for 72 h, the reaction mixture is neutralized with phosphate buffer solution and extracted with dichloromethane. The aqueous layer is concentrated and the residue is leached with a boiling mixture of ethyl acetate and methanol. The organic solvents are removed to obtain 90 mg of the file compound as a yellowish foam.

EF: $C_{22}H_{23}NO_5$; MW: 381.43

MS: 382.4 (MH⁺)

M.p.: 172-183° C.

Alternative Procedure:

A solution of 5.68 g of acetic acid (2RS,4aRS,10bRS)-6-(4-methoxycarbonylphenyl)-8,9-dimethoxy-(1,2,3,4,4a, 10b)-hexahydrophenanthridin-2-yl ester (compound D1) in 250 ml of methanol is treated at boiling temperature with a solution of 2.0 g of sodium hydroxide in 15 ml of water comprising a catalytic amount of hydrogen peroxide (30% strength). Stirring is continued for 1.5 h under reflux, the reaction mixture is cooled and treated with halfconcentrated aqueous hydrochloric acid to adjust to pH 6-7. The solvents are evaporated and the residue is dried in vacuo to obtain 8.1 g of a yellowish solid, which can be used without further purification in the next step. The free acid is obtained by leaching the residue with boiling chloroform and concentration of the resulting chloroform solution.

C2. 4-[(2RS,4aRS,10bRS)-2-Acetoxy-9-(1,1-difluoro-methoxy)-8-methoxy-1,2,3,4,4a,10b-hexahydro-phenanthridin-6-yl]-benzoic Acid Methyl Ester 500 mg of N-{(1RS,2RS,4RS)-4-acetoxy-2-[3-(1,1-difluoro-methoxy)-4-methoxy-phenyl]-cyclohexyl}-terephthalamic acid methyl ester (compound D2) are dissolved in 2 ml of phosphorus oxychloride and heated for 4.5 h at 100° C. After cooling to room temperature the sample is diluted with 10 ml of dichloromethane and added dropwise to an aqueous sodium hydroxide solution. The water layer is extracted twice with dichloromethane. The solvent is removed and the crude product purified by chromatography on silica gel to give 310 mg of the title compound as a colourless foam.

EF: $C_{25}H_{25}F_2NO_6$; MW: 473.48

MS: 474.2 (MH⁺)

D1. Acetic Acid (2RS,4aRS,10bRS)-6-(4-methoxy-carbonylphenyl)-8,9-dimethoxy-(1,2,3,4,4a,10b)-hexahydrophenanthridin-2-yl ester 10.8 g of phosphorus pentachloride are suspended in 170 ml of isopropyl acetate, 8.1 g of acetic acid (1RS,3RS,4RS)-4-{[1-(4-methoxycarbonylphenyl)methanoyl]amino}-3-(3,4-dimethoxyphenyl)cyclohexyl ester (compound E1) dissolved 100 ml are added and the mixture is stirred. When reaction is complete, a mixture of 100 ml of triethylamine and 100 ml of isopropyl acetate is added dropwise at 0° C. After diluting with 80 ml water at 0° C. and phase separation, the aqueous phase is extracted three times with each 60 ml of dichloromethane. The organic phases are dried using magnesium sulfate. After concentrating, the residue is recrystallized from ethyl acetate/cyclohexane to give 5.68 g of the title compound.

EF: $C_{25}H_{27}NO_6$; MW: 437.50
MS: 438.3 (MH$^+$)
$R_f$=0.62 (petroleum ether/ethyl acetate/triethylamine=6/3/1)
M.p.: 184-185° C.

D2. N-((1RS,2RS,4RS)-4-Acetoxy-2-[3-(1,1-difluoro-methoxy)-4-methoxy-phenyl]-cyclohexyl) terephthalamic Acid Methyl Ester The title compound is prepared analogously as described in Example E1 starting from compound E2.
EF: $C_{25}H_{27}F_2NO_7$; MW: 491.49
MS: 492.0 (MH$^+$)

E1. Acetic Acid (1RS,3RS,4RS)-4-{[1-(4-methoxy-carbonylphenyl)methanoyl]amino}-3-(3,4-dimethoxyphenyl)cyclohexyl Ester 1.6 g of acetic acid (1RS,3RS,4RS)-4-amino-3-(3,4-dimethoxyphenyl)cyclohexyl ester (compound F1) are dissolved in 30 ml of dichloromethane. 982 mg (5.45 mmol) of terephthalic acid monomethyl ester and 1.25 g (6.74 mmol) of N-ethyl-N'-(3-dimethylaminopropyl)carbodiimide hydrochloride are added successively under stirring. After 3 h further 18 mg (0.1 mmol) of terephthalic acid monomethyl ester are added. After 15 h the reaction is treated with aqueous hydrochloric acid and extracted several times with dichloromethane. After evaporation of the combined organic phases, the crude product is crystallized from ethyl acetate/cyclohexane to give 1.87 g (73% of theory) of the title compound as colourless solid.

EF: $C_{25}H_{29}NO_7$; MW: 455.51
MS: 456.2 (MH$^+$)
$R_f$=0.69 (ethyl acetate/triethylamine=9/1)

Starting from the appropriate compound F1 or E2 to E7, and the appropriate benzoic acid derivative further compounds according to this invention can be obtained according to the procedure as in Example E1 or analogously or similarly thereto.

E2. Acetic Acid (1RS,3RS,4RS)-4-amino-3-[3-(1,1-difluoro-methoxy)-4-methoxy-phenyl]-cyclohexyl Ester The title compound is prepared analogously as described in Example F1 starting from compound F2.
EF: $C_{16}H_{21}F_2NO_4$; MW: 329.35
MS: 330.0 (MH$^+$)

E3. Acetic Acid (1RS,3RS,4RS)-4-amino-3-(3-ethoxy-4-methoxy-phenyl)-cyclohexyl Ester Starting from compound F3 mentioned below, the title compound is obtained analogously to the procedure as in Example F1.
EF: $C_{17}H_{25}NO_4$; MW: 307.39
MS: 308.0 (MH$^+$)

E3a. Acetic Acid (1R,3R,4R)-4-amino-3-(3-ethoxy-4-methoxy-phenyl)-cyclohexyl Ester 24.0 g (55.0 mmol) of the pyroglutamate of the title compound (compound E3b) are suspended in 150 ml of water, 100 ml of dichloromethane are added, then saturated $KHCO_3$-solution until the gas evolution ceased. After phase separation, reextraction of the water layer and drying the combined organic layers with sodium sulfate the solvent is removed to give 16.9 g of the salt-free title compound.

Analytical Column Chromatography (CHIRALPAK AD-H 250×4.6 mm 5µ No. ADHOCE-DB030, Eluent: n-Hexan/iPrOH=80/20 (v/v)+0.1% Diethylamine): Retention Time: 6.54 min

E3b. Acetic Acid (1R,3R,4R)-4-amino-3-(3-ethoxy-4-methoxy-phenyl)-cyclohexyl Ester, Salt with L-pyroglutamic Acid Solution A: 55.2 g (180 mmol) of racemic acetic acid (1RS,3RS,4RS)-4-amino-3-(3-ethoxy-4-methoxyphenyl)-cyclohexyl ester (compound E3) are dissolved in 540 ml of isopropyl acetate.

Solution B: 18.6 g (144 mmol) of L-pyroglutamic acid are dissolved in 260 ml of isopropanol under heating, then 290 ml of isopropyl acetate is added carefully.

Solution B is added to solution A and left for 48 hours. The solid is filtered off and washed with a little isopropyl acetate to give after drying 32.48 g colorless crystals with a ratio of the enantiomers of 97:3 in favour of the title compound.

M.p.: 165-167° C.

E4. Acetic Acid (1RS,3RS,4RS)-4-amino-3-[4-(1,1-difluoro-methoxy)-3-methoxy-phenyl]-cyclohexyl Ester Starting from compound F4 mentioned below, the title compound is obtained according to the procedure as in Example F1.
EF: $C_{16}H_{21}F_2NO_4$; MW: 329.35
MS: 330.0 (MH$^+$)

E5. Acetic Acid (1RS,3RS,4RS)-4-amino-3-[3-(2,2-difluoro-ethoxy)-4-methoxy-phenyl]-cyclohexyl Ester Starting from compound F5 mentioned below, the title compound is obtained according to the procedure as in Example F1.

E5a. Acetic Acid (1R,3R,4R)-4-amino-3-[3-(2,2-difluoro-ethoxy)-4-methoxy-phenyl]-cyclohexyl Ester The title compound is obtained from its pyroglutamate salt (compound E5b) analogously as described for compound E3a using sodium hydrogencarbonate solution.

E5b. Acetic Acid (1R,3R,4R)-4-amino-3-[3-(2,2-difluoro-ethoxy)-4-methoxy-phenyl]-cyclohexyl Ester, Salt with L-pyroglutamic Acid 343 mg (1.00 mmol) of acetic acid (1RS,3RS,4RS)-4-amino-3-[3-(2,2-difluoro-ethoxy)-4-methoxyphenyl]-cyclohexyl ester (compound E5) are dissolved in 3 ml of isopropanol. A solution of 103 mg (0.80 mmol) of L-pyroglutamic acid in 2 ml of isopropanol is added. After filtering and drying 162 mg of the pyroglutamate are isolated with an enantiomeric ratio of 97:3 in favour of the title compound.

E6. Acetic Acid (1SR,3RS,4RS)-3-amino-4-(3-ethoxy-4-methoxy-phenyl)-cyclohexyl Ester 3.0 g (7.36 mmol) of acetic acid (1SR,3RS,4RS)-3-tert-butoxycarbonylamino-4-(3-ethoxy-4-methoxyphenyl)-cyclohexyl ester (compound F6) are dissolved in 6 ml of 4 M HCl in dioxane and stirred for 30 min. After removal of the solvent the residue is dissolved in dichloromethane and 25 ml of sat. NaHCO$_3$ solution are added carefully. After phase separation, reextraction of the water layer and drying of the combined organic layers (Na$_2$SO$_4$) the solvent is removed to give 2.25 g of the title compound.

EF: C17H25N O4; MW: 307.39

MS: 308.1 (MH$^+$)

E7. Acetic Acid (1SR,3RS,4RS)-3-amino-4-(3,4-dimethoxy-phenyl)-cyclohexyl Ester The title compound can be obtained from compound F7 analogously as described for compound E6.

F1. Acetic Acid (1RS,3RS,4RS)-4-amino-3-(3,4-dimethoxyphenyl)cyclohexyl Ester A solution of 10.37 g of acetic acid (1RS,3RS,4RS)-3-(3,4-dimethoxyphenyl)-4-nitrocyclohexyl ester (compound G1) in 240 ml of ethanol is added to a zinc-copper couple, prepared from 16.8 g of zinc powder and 920 mg of copper (II) acetate monohydrate in acetic acid, the resulting suspension is refluxed and treated with 26 ml of acetic acid, 3.2 ml of water and 26 ml of ethanol. The resulting mixture is refluxed for further 15 min. The precipitate is filtered off with suction and the solvent is removed. Chromatographical purification on silica gel using a mixture of petroleum ether/ethyl acetate/triethylamine in the ratio 2/7/1 and concentration of the corresponding eluate fractions afford 5.13 g (55% of theory) of the title compound as a pale brown oil.

R$_f$=0.35 (petroleum ether/ethyl acetate/triethylamine=2/7/1)

F2. Acetic Acid (1RS,3RS,4RS)-3-[3-(1,1-difluoro-methoxy)-4-methoxy-phenyl]-4-nitrocyclohexyl Ester The title compound is prepared analogously as described in Example G1 starting from compound G2.

Starting from the appropriate compound G3 to G5 mentioned below, the following compounds F3 to F5 are obtained according to the procedure as in Example G1.

F3. Acetic Acid (1RS,3RS,4RS)-3-(3-ethoxy-4-methoxy-phenyl)-4-nitrocyclohexyl Ester

F4. Acetic Acid (1RS,3RS,4RS)-3-[4-(1,1-difluoro-methoxy)-3-methoxy-phenyl]-4-nitrocyclohexyl Ester

F5. Acetic Acid (1RS,3RS,4RS)-3-[3-(2,2-difluoro-ethoxy)-4-methoxy-phenyl]-4-nitrocyclohexyl Ester

F6. Acetic Acid (1SR,3RS,4RS)-3-tert-butoxycarbonylamino-4-(3-ethoxy-4-methoxy-phenyl)-cyclohexyl Ester 22.64 g (65 mmol) of [(1RS,6RS)-6-(3-ethoxy-4-methoxy-phenyl)-cyclohex-3-enyl]-carbamic acid tert-butyl ester (compound G6) are dissolved in 180 ml of THF and 50 ml of BH$_3$ (1 M solution in THF) are added dropwise (30 min). After stirring for 2 h the mixture is cooled using an ice bath and a mixture of 30 ml of H$_2$O$_2$ (30%) and 60 ml of aqueous NaOH (3 M) is added. The mixture is stirred for 30 min at room temperature. 400 ml of water and 200 ml of dichloromethane are added. After phase separation, reextraction of the water layer and drying of the combined organic layers (Na$_2$SO$_4$) the solvent is removed and the crude product (23.42 g, mixture of the two mentioned regioisomers~2:1 in favour of the title compound) is used directly without further purification.

The crude material from above then is dissolved in 50 ml of pyridine. 50 mg of 4-dimethylaminopyridine and 60 ml of acetic anhydride are added and the mixture stirred for 90 min at 100° C. The solvents and the acetic anhydride are removed (sat. NaHCO$_3$ solution). Purification by means of chromatography yields 9.4 g of the title compound as colorless foam.

EF: C22H33N O6; MW: 407.51

MS: 308.1 (MH$^+$-Boc), 407.8 (MH$^+$), 430.1 (MNa$^+$)

F7. Acetic Acid (1SR,3RS,4RS)-3-tert-butoxycarbonylamino-4-(3,4-dimethoxy-phenyl)cyclohexyl Ester The title compound can be obtained from compound G7 analogously as described for compound F6.

G1. Acetic Acid (1RS,3RS,4RS)-3-(3,4-dimethoxyphenyl)-4-nitrocyclohexyl Ester 10.18 g of (1RS,3RS,4RS)-3-(3,4-dimethoxyphenyl)-4-nitrocyclohexanol (compound H1) are dissolved in 100 ml of acetic anhydride and the solution is heated to 100° C. for 1-2 h. After removal of the solvent, the residue is chromatographed on silica gel using a mixture of petroleum ether/ethyl acetate in the ratio 2/1. Concentration of the corresponding eluate fractions furnish 10.37 g (89% of theory) of the title compound as an oil.

R$_f$=0.32 (petroleum ether/ethyl acetate=2/1)

G2. (1RS,3RS,4RS)-3-[3-(1,1-Difluoro-methoxy)-4-methoxy-phenyl]-4-nitrocyclohexanol The title compound is prepared analogously as described in Example H1 starting from compound H2.

Starting from the appropriate compound H3 to H5 mentioned below, the following compounds G3 to G5 are obtained according to the procedure as in Example H1.

G3. (1RS,3RS,4RS)-3-(3-Ethoxy-4-methoxy-phenyl)-4-nitrocyclohexanol

G4. (1RS,3RS,4RS)-3-[4-(1,1-Difluoro-methoxy)-3-methoxy-phenyl]-4-nitrocyclohexanol G5. (1RS,3RS,4RS)-3-[3-(2,2-Difluoro-ethoxy)-4-methoxy-phenyl]-4-nitrocyclohexanol G6. [(1RS,6RS)-6-(3-Ethoxy-4-methoxy-phenyl)-cyclohex-3-enyl]-carbamic Acid Tert-Butyl Ester Starting from (1RS,6RS)-6-(3-ethoxy-4-methoxy-phenyl)-cyclohex-3-enylamine (compound H6) the title compound is obtained analogously as described for compound G7.
EF: C20H29N O4; MW: 347.46,
MS: 370.1 (MNa$^+$)

G7. [(1RS,6RS)-6-(3,4-Dimethoxy-phenyl)-cyclohex-enyl]-carbamic Acid Tert-Butyl Ester 15.18 g (65.06 mmol) of (±)-cis-6-(3,4-dimethoxyphenyl)-cyclohex-3-enylamine (compound H7) and 14.21 g (65.11 mmol) of Boc$_2$O are stirred in dichloromethane for 2.5 h, then the solvent is removed and the residue crystallized from ethylacetate/n-heptane to give 19.1 g of the title compound.
EF: C19H27N O4; MW: 333.43,
MS: 334.2 (MH$^+$)

H1. (1RS,3RS,4RS)-3-(3,4-Dimethoxyphenyl)-4-nitrocyclohexanol 10 g of (1RS,3RS,4SR)-3-(3,4-dimethoxyphenyl)-4-nitrocyclohexanol (compound I1) are dissolved in 170 ml of absolute 1,2-dimethoxyethane. 14.3 ml of a 30% solution of sodium methanolate in methanol are added dropwise. After complete addition, stirring is continued for 10 min and a mixture consisting of 85% phosphoric acid and methanol is added to pH 1. By adding of saturated potassium hydrogencarbonate solution the resulting suspension is neutralized. The mixture is diluted with water and dichloromethane, the organic layer is separated and extracted with dichloromethane. The solvents are removed under reduced pressure to yield the title compound as a pale yellow oil, which crystallizes. The title compound is used without further purification in the next step.
R$_f$=0.29 (petroleum ether/ethyl acetate=1/1)
M.p.: 126-127° C.

H2. (1RS,3RS,4SR)-3-[3-(1,1-Difluoro-methoxy)-4-methoxy-phenyl]-4-nitrocyclohexanol The title compound is prepared analogously as described in Example I1 starting from compound I2. Starting from the appropriate compound I3 to I5 mentioned below, the following compounds H3 to H5 are obtained according to the procedure as in Example I1.

H3. (1RS,3RS,4SR)-3-(3-Ethoxy-4-methoxy-phenyl)-4-nitrocyclohexanol

H4. (1RS,3RS,4SR)-3-[4-(1,1-Difluoro-methoxy)-3-methoxy-phenyl]-4-nitrocyclohexanol H5. (1RS,3RS,4SR)-3-[3-(2,2-Difluoro-ethoxy)-4-methoxy-phenyl]-4-nitrocyclohexanol H6. (1RS,6RS)-6-(3-Ethoxy-4-methoxy-phenyl)-cyclohex-3-enylamine Starting from 2-ethoxy-1-methoxy-4-((1RS,6RS)-6-nitro-cyclohex-3-enyl)-benzene (compound I6) the title compound is obtained analogously as described for compound H7.

H7. (±)-cis-6-(3,4-Dimethoxyphenyl)-cyclohex-3-enylamine 40 g of (±)-cis-1,2-dimethoxy-4-(2-nitrocyclohex-4-enyl) benzene (compound I7) are dissolved in 400 ml of ethanol and 40 g of zinc powder are added. After heating to boiling temperature, 65 ml of glacial acetic acid are added dropwise. Afterwards, the reaction mixture is filtrated and concentrated. The residue is redissolved in diluted hydrochloric acid and extracted with toluene. The aqueous layer is alkalized using 6 N solution of sodium hydroxide and extracted several times with toluene. The combined organic phases of the alkalic extraction are dried using sodium sulfate and concentrated. The residue is chromatographed on silica gel. 11.5 g of the title compound are obtained.

I1. (1RS,3RS,4SR)-3-(3,4-Dimethoxyphenyl)-4-nitrocyclohexanol

Under nitrogen atmosphere 16.76 g of (3RS,4SR)-3-(3,4-dimethoxyphenyl)-4-nitrocyclohexanone (compound J1) are dissolved in 300 ml of tetrahydrofurane, the solution is cooled to −78° C., and 75 ml of 1 M solution of potassium tri-sec-butylborohydride in tetrahydrofurane is added dropwise. After stirring for further 1 h, a mixture consisting of 30% hydrogeneperoxide solution and phosphate buffer solution is added. Stirring is continued for further 10 min, the reaction mixture is diluted with 400 ml of ethyl acetate and the aqueous layer is extracted with ethyl acetate, the combined organic phases are concentrated to give a foam, which is purified by chromatography on silica gel using a mixture of petroleum ether/ethyl acetate in the ratio 1/1 to furnish 10.18 g (60% of theory) of the title compound.
EF: C$_{14}$H$_{19}$NO$_5$; MW: 281.31
MS: 299.1 (MNH$_4^+$)
R$_f$=0.29 (petroleum ether/ethyl acetate=1/1)
M.p.: 139-141° C.

I2. (3RS,4SR)-3-[3-(1,1-Difluoro-methoxy)-4-methoxy-phenyl]-4-nitrocyclohexanone The title compound is prepared analogously as described in Example J1 starting from compound J2.

Starting from the appropriate compound J3 to J5 mentioned below, the following compounds I3 to I5 are obtained according to the procedure as in Example J1.

I3. (3RS,4SR)-3-(3-Ethoxy-4-methoxy-phenyl)-4-nitrocyclohexanone

I4. (3RS,4SR)-3-[4-(1,1-Difluoro-methoxy)-3-methoxy-phenyl]-4-nitrocyclohexanone I5. (3RS,4SR)-3-[3-(2,2-Difluoro-ethoxy)-4-methoxy-phenyl]-4-nitrocyclohexanone I6. 2-Ethoxy-1-methoxy-4-((1RS,6RS)-6-nitro-cyclohex-3-enyl)-benzene Starting from 2-ethoxy-1-methoxy-4-((1RS,6SR)-6-nitro-cyclohex-3-enyl)-benzene (compound J6) the title compound is obtained analogously as described for compound I7.

I7. (±)-cis-1,2-Dimethoxy-4-(2-nitrocyclohex-4-enyl)benzene 10.0 g of (±)-trans-1,2-dimethoxy-4-(2-nitrocyclohex-4-enyl)benzene (compound J7) and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized in ethanol. 8.6 g of the title compound of m.p. 82.5-84° C. are obtained.

J1. (3RS,4SR)-3-(3,4-Dimethoxyphenyl)-4-nitrocyclohexanone 90.0 g of 3,4-dimethoxy-ω-nitrostyrene (compound K1), 90 ml of 2-trimethylsilyloxy-1,3-butadiene and 180 ml of abs. toluene are put in an autoclave, where the mixture is stirred at 140° C. for 2 days and then cooled. After addition of 1000 ml of ethyl acetate, 300 ml of a 2 N solution of hydrochloric acid are dropped under stirring. The phases are separated and the aqueous layer is extracted three times with dichloromethane. The combined organic extracts are washed with saturated sodium hydrogencarbonate solution, dried over magnesium sulfate and the solvents are removed under reduced pressure to give 150 g of the crude title compound. Further purification is carried out by chromatography on silica gel using petroleum ether/ethyl acetate in the ratio 1/1 as eluent to give 81.5 g (67% of theory) of the pure title compound.
EF: $C_{14}H_{17}NO_5$; MW: 279.30
MS: 279 ($M^+$), 297.1 ($MNH_4^+$)
$R_f$=0.47 (petroleum ether/ethyl acetate=1/1)
M.p.: 147-148° C.

Starting from starting compounds, which are art-known or which can be obtained according to known procedures, such as e.g. as described in WO 95/01338 or analogously or similarly thereto, the following compounds J2 to J4 are obtained according to the procedure as in Example K1:

J2. 3-(1,1-Difluoro-methoxy)-4-methoxy-ω-nitrostyrene

J3. 3-Ethoxy-4-methoxy-ω-nitrostyrene

J4. 4-(1,1-Difluoro-methoxy)-3-methoxy-ω-nitrostyrene

J5. 3-(2,2-Difluoro-ethoxy)-4-methoxy-ω-nitrostyrene

The title compound is obtained starting from 3-(2,2-difluoro-ethoxy)-4-methoxy-benzaldehyde (compound K2) according to the procedure as in Example K1.
M.p.: 164-165° C.

J6. 2-Ethoxy-1-methoxy-4-((1RS,6SR)-6-nitro-cyclohex-3-enyl)-benzene

Starting from 3-ethoxy-4-methoxy-m-nitrostyrene (compound J3) the title compound is obtained analogously as described for compound J7.

J7. (±)-trans-1,2-Dimethoxy-4-(2-nitrocyclohex-4-enyl)benzene 50.0 g of 3,4-dimethoxy-ω-nitrostyrene (compound K1), and 1.0 g (9.1 mmol) of hydroquinone are suspended in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5-115.5° C.

K1. 3,4-Dimethoxy-ω-nitrostyrene 207.0 g of 3,4-dimethoxybenzaldehyde, 100.0 g of ammonium acetate and 125 ml of nitromethane are heated to boiling for 3-4 h in 1.0 l of glacial acetic acid. After cooling in an ice bath, the precipitate is filtered off with suction, rinsed with glacial acetic acid and petroleum ether and dried. M.p.: 140-141° C.

Yield: 179.0 g.

K2. 3-(2,2-Difluoro-ethoxy)-4-methoxy-benzaldehyde 10.04 g of isovanillin and 15.5 g of potassium carbonate are placed in an autoclave. 50 ml of DMF are added as well as 12.44 g of 2-bromo-1,1-difluoroethane. The autoclave is closed and heated at 60° C. for 20 h. Then the solids are filtered off and washed with 120 ml of DMF. About 120 ml of the solvent are distilled off and the residue poured on 200 ml of ice/water, where the product precipitates. After stirring the slurry for 30 minutes the product is filtered off and dried to give 13.69 g of the desired product.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus, diabetes mellitus, leukaemia, osteoporosis and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia; as well as for enhancing cognition.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions for treating disorders which are mediated by phosphodiesterases, in particular PDE4-mediated disorders, such as, for example, those mentioned in the specification of this invention or those which are apparent or known to the skilled person.

The invention also relates to the use of the compounds according to the invention for the manufacture of pharmaceutical compositions having PDE4 inhibitory activity.

The invention furthermore relates to pharmaceutical compositions for the treatment and/or prophylaxis of the illnesses mentioned, which contain one or more of the compounds according to the invention.

The invention yet furthermore relates to compositions comprising one or more compounds according to this invention and a pharmaceutically acceptable carrier. Said compositions can be used in therapy, such as e.g. for treating, preventing or ameliorating one or more of the abovementioned diseases.

The invention still yet furthermore relates to pharmaceutical compositions according to this invention having PDE, particularly PDE4, inhibitory activity.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula 1 according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarily between 0.01 and 3 mg per day. The customary dose in the case of systemic therapy (p.o. or i.v.) is between 0.003 and 3 mg/kg per day. In another embodiment, the dose for administration by inhalation is between 0.1 and 3 mg per day, and the dose in the case of systemic therapy (p.o. or i.v.) is between 0.03 and 3 mg/kg per day.

Biological Investigations

The second messenger cyclic AMP (CAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (J E Souness et al., Immunopharmacology 47:127-162, 2000).

The antiinflammatory potential of PDE4 inhibitors in vivo in various animal models has been described (M M Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therap 12: 377-386, 1999). In addition, the immunomodulatory potential of PDE4 inhibitors is evident from the inhibition of T-cell responses like cytokine synthesis or proliferation (D M Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Methods for Measuring Inhibition of PDE4 Activity

The PDE4B2 (GB no. M97515) was a gift of Prof. M. Conti (Stanford University, USA). It was amplified from the original plasmid (pCMV5) via PCR with primers Rb9 (5'-GC-CAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmid was cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatant was selected using plaque assay methods. After that, high-titre virus supernatant was prepared by amplifying 3 times. PDE was expressed in SF21 cells by infecting $2 \times 10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at –0° C. until subsequent use (see below). The protein content was determined by the Bradford method (BioRad, Munich) using BSA as the standard.

PDE4B2 activity is inhibited by the said compounds in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg of BSA (bovine serum albumin)/ml, 5 mM $Mg^{2+}$, 0.5 µM cAMP (including about 50,000 cpm of [3H]cAMP), 1 µl of the respective substance dilution DMSO and sufficient recombinant PDE (1000×g supernatant, see above) to ensure that 10-20% of the cAMP is converted under the said experimental conditions. The final concentration of DMSO in the assay (1% v/v) does not substantially affect the activity of the PDE investigated. After a preincubation of 5 min at 37° C., the reaction is started by adding the substrate (CAMP) and the assay is incubated for a further 15 min; after that, it is stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression. Representative inhibitory values determined for the compounds according to the invention follow from the following table A, in which the numbers of the compounds correspond to the numbers of the Examples.

TABLE A

Inhibition of the PDE4 activity

| Compound | $-\log IC_{50}$ |
|---|---|
| 1 | The inhibitory values |
| 2 | of these listed |
| 3 | compounds are |
| 4 | higher than 7.5 |
| 5 | |
| 6 | |

The invention claimed is:

1. A compound of formula 1

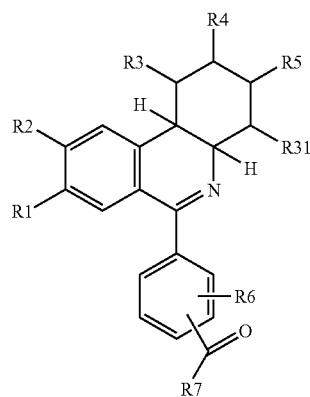

(1)

in which

R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy, or in which R1 and R2 together are a 1-2C-alkylenedioxy group, R3 is hydrogen or 1-4C-alkyl, R31 is hydrogen or 1-4C-alkyl, either, in a first embodiment (embodiment a), R4 is —O—R41, in which R41 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl, and R5 is hydrogen or 1-4C-alkyl, or, in a second embodiment (embodiment b), R4 is hydrogen or 1-4C-alkyl, and R5 is —O—R51, in which R51 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl, R6 is hydrogen, halogen, nitro, 1-4C-alkyl, trifluoromethyl or 1-4C-alkoxy, R7 is a radical of formulae (a), (b) or (c)

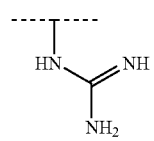

(a)

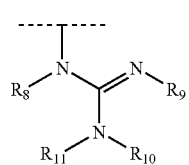

(b)

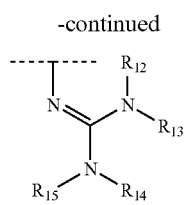

in which
if R7 is a radical of the formula (b),
either
R8 and R9 independently of one another are hydrogen, 1-7C-alkyl, 3-7C-cycloalkyl, 3-7C-cycloalkylmethyl, cyano, hydroxy-2-4C-alkyl, 1-4C-alkoxy-2-4C-alkyl or R28,
and R10 and R11 independently of one another are hydrogen, 1-7C-alkyl, or 3-7C-cycloalkyl,
or
R8 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28,
R9 is hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and
R10 and R11, together and including the nitrogen atom to which both are bonded, are a azocan-1-yl or a piperazin-1-yl radical substituted in 4-position by R19,
if R7 is a radical of the formula (c),
either
R12 and R13 independently of one another are hydrogen, 1-7C-alkyl, 3-7C-cycloalkyl, 3-7C-cycloalkylmethyl, hydroxy-2-4C-alkyl, 1-4C-alkoxy-2-4C-alkyl or R28,
and R14 and R15 independently of one another are hydrogen, 1-7C-alkyl, or 3-7C-cycloalkyl,
or
R12 and R13 independently of one another are hydrogen, 1-7C-alkyl, 3-7C-cycloalkyl, 3-7C-cycloalkylmethyl, hydroxy-2-4C-alkyl, 1-4C-alkoxy-2-4C-alkyl or R28, and
R14 and R15, together and including the nitrogen atom to which both are bonded, are a azocan-1-yl, or a piperazin-1-yl radical substituted in 4-position by R19,
or
R12 and R13, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl, 2,6-dimethyl-piperidin-1-yl, 4-benzyl-piperidin-1-yl or thiomorpholin-4-yl radical, and
R14 and R15, together and including the nitrogen atom to which both are bonded, are a 4-(1-4C-alkyl-)-piperazin-1-yl radical,
R19 is 1-4C-alkyl, formyl, 3-7C-cycloalkyl, 3-7C-cycloalkylmethyl, 1-4C-alkoxycarbonyl-1-4C-alkyl, 1-4C-alkylcarbonyl, hydroxy-2-4C-alkyl, 1-4C-alkoxy-2-4C-alkyl, hydroxy-2-4C-alkoxy-2-4C-alkyl, 1-4C-alkoxy-2-4C-alkoxy-2-4C-alkyl, phenyl, phenyl substituted by R24 and/or R25, [benzo(1,3)dioxol]-5-ylmethyl, phenyl-1-4C-alkyl or phenyl-1-4C-alkyl substituted in the phenyl moiety by R26 and/or R27,
R24 is halogen, nitro, carboxyl, 1-4C-alkyl, 1-4C-alkylcarbonyl, trifluoromethyl or 1-4C-alkoxy,
R25 is halogen, 1-4C-alkyl or 1-4C-alkoxy,
R26 is halogen, nitro, carboxyl, 1-4C-alkyl, trifluoromethyl or 1-4C-alkoxy,
R27 is halogen, 1-4C-alkyl or 1-4C-alkoxy,
R28 is R29(R30)N-2-4C-alkyl wherein
R29 and R30, together and including the nitrogen atom to which both are bonded, are a pyrrolidin-1-yl, piperidin-1-yl, piperazin-1-yl, 4-(1-4C-alkyl-)piperazin-1-yl, azepan-1-yl, azocan-1-yl, azonan-1-yl, azecan-1-yl, tetrahydroisoquinolin-2-yl, tetrahydro-6,7-dimethoxyisoquinolin-2-yl, 3,5-dimethyl-pyrazol-1-yl, pyrazol-1-yl, morpholin-4-yl, 2,6-dimethyl-morpholin-4-yl, 2,6-dimethyl-piperidin-1-yl, 4-benzyl-piperidin-1-yl, thiomorpholin-4-yl or 1H-1,2,4-triazol-1-yl radical, or a salt, N-oxide, salt of the N-oxide, enantiomer, salt of the enantiomer, E/Z isomer, salt of the E/Z isomer, tautomer or salt of the tautomer thereof.

2. A compound of formula 1 according to claim 1 in which
R1 is 1-2C-alkoxy, 3-5C-cycloalkoxy, 3-5C-cycloalkylmethoxy, 2,2-difluoroethoxy, or completely or predominantly fluorine-substituted 1-2C-alkoxy,
R2 is 1-2C-alkoxy, 3-5C-cycloalkoxy, 3-5C-cycloalkylmethoxy, 2,2-difluoroethoxy, or completely or predominantly fluorine-substituted 1-2C-alkoxy,
R3 is hydrogen,
R31 is hydrogen,
either, in a first embodiment (embodiment a),
R4 is —O—R41, in which
R41 is hydrogen or 1-4C-alkylcarbonyl, and
R5 is hydrogen,
or, in a second embodiment (embodiment b),
R4 is hydrogen, and
R5 is —O—R51, in which
R51 is hydrogen or 1-4C-alkylcarbonyl,
R6 is hydrogen, halogen, nitro, 1-4C-alkyl, trifluoromethyl or 1-4C-alkoxy,
R7 is a radical of formulae (a), (b) or (c)

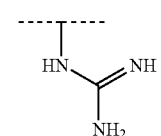

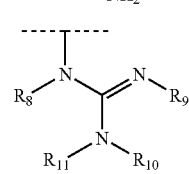

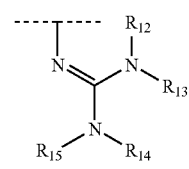

in which
if R7 is a radical of the formula (b),
either
R8 is hydrogen,
R9 is hydrogen, 1-4C-alkyl, 3-7C-cycloalkyl or 3-7C-cycloalkylmethyl, and R10 and R11 independently of one another are hydrogen, 1-4C-alkyl, or 3-7C-cycloalkyl, or R8 is hydrogen, R9 is hydrogen, 1-4C-alkyl, 3-7C-cycloalkyl or 3-7C-cycloalkylmethyl, and R10 and R11, together and including the nitrogen atom to which both are bonded, are a azocan-1-yl or a piperazin-1-yl radical substituted in 4-position by R19, if R7 is a radical of the formula (c), either R12 and R13 independently of one another are hydrogen, 1-4C-alkyl, 3-7C-cycloalkyl or 3-7C-cycloalkylmethyl, and R14 and R15 independently of one another are hydrogen, 1-4C-alkyl, or 3-7C-cycloalkyl, or R12 and R13 independently of one another are hydrogen, 1-4C-alkyl, 3-7C-cycloalkyl or 3-7C-cycloalkylmethyl, and R14 and R15, together and including the nitrogen atom to which both are bonded, are a azocan-1-yl or a piperazin-1-yl radical substituted in 4-position by R19, or R12 and R13, together and including the nitrogen atom to which both are bonded, are a pyrrolidin-1-yl, piperidin-1-yl, azepan-1-yl, morpholino-4-yl, 4-(1-4C-alkyl-)-piperazin-1-yl, 2,6-dimethyl-morpholin-4-yl or 2,6-dimethyl-piperidin-1-yl radical, and R14 and R15, together and including the nitrogen atom to which both are bonded, are a 4-(1-4C-alkyl-)-piperazin-1-yl radical, R19 is 1-4C-alkyl, formyl, 1-4C-alkylcarbonyl, 2-hydroxyethyl, phenyl, phenyl substituted by R24 and/or R25, phenyl-1-4C-alkyl or phenyl-1-4C-alkyl substituted in the phenyl moiety by R26 and/or R27, R24 is halogen, nitro, carboxyl, 1-4C-alkyl or 1-4C-alkoxy, R25 is halogen, 1-4C-alkyl or 1-4C-alkoxy, R26 is halogen, nitro, 1-4C-alkyl or 1-4C-alkoxy, R27 is halogen, 1-4C-alkyl or 1-4C-alkoxy, or a salt, N-oxide, salt of the N-oxide, enantiomer, salt of the enantiomer, E/Z isomer, salt of the E/Z isomer, tautomer or salt of the tautomer thereof.

3. A compound of formula 1 according to claim 1 in which

R1 is 1-2C-alkoxy, 2,2-difluoroethoxy, or completely or predominantly fluorine-substituted 1-2C-alkoxy, R2 is 1-2C-alkoxy, 2,2-difluoroethoxy, or completely or predominantly fluorine-substituted 1-2C-alkoxy, R3 is hydrogen, R31 is hydrogen, either, in a first embodiment (embodiment a), R4 is —O—R41, in which R41 is hydrogen or 1-4C-alkylcarbonyl, and R5 is hydrogen, or, in a second embodiment (embodiment b), R4 is hydrogen, and R5 is —O—R51, in which R51 is hydrogen or 1-4C-alkylcarbonyl, R6 is hydrogen, R7 is a radical selected from

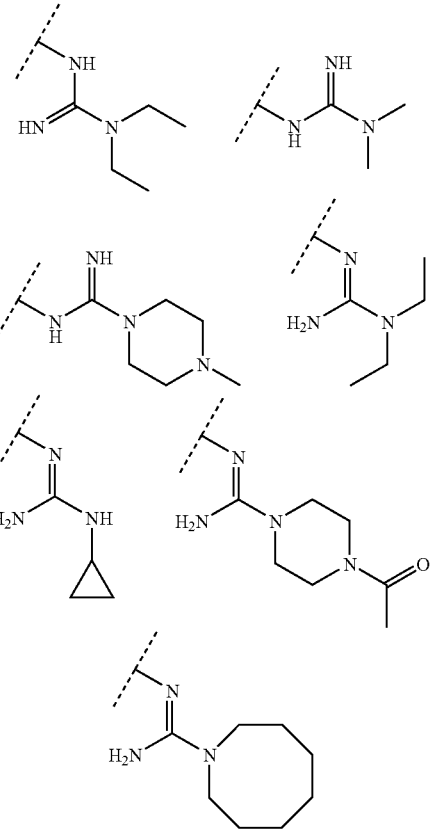

or a salt, N-oxide, salt of the N-oxide, enantiomer, salt of the enantiomer, E/Z isomer, salt of the E/Z isomer, tautomer or salt of the tautomer thereof.

4. A compound of formula 1 according to claim 1 in which

R1 is 1-2C-alkoxy, or completely or predominantly fluorine-substituted 1-2C-alkoxy, R2 is 1-2C-alkoxy, or predominantly fluorine-substituted 1-2C-alkoxy, R3 is hydrogen, R31 is hydrogen, R4 is —O—R41, in which R41 is hydrogen or 1-4C-alkylcarbonyl, and R5 is hydrogen, R6 is hydrogen, R7 is a radical of formula (c)

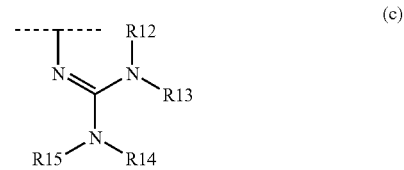

in which either

R12 is hydrogen,

R13 is hydrogen,

R14 is hydrogen or 1-4C-alkyl, and
R15 is 1-4C-alkyl or 3-7C-cycloalkyl, or

R12 is hydrogen,
R13 is hydrogen, and
R14 and R15, together and including the nitrogen atom to which both are bonded, are a azocan-1-yl or a piperazin-1-yl radical substituted in 4-position by R19, in which
R19 is 1-4C-alkylcarbonyl, or a salt, N-oxide, salt of the N-oxide, enantiomer, salt of the enantiomer, E/Z isomer, salt of the E/Z isomer, tautomer or salt of the tautomer thereof.

5. A compound of formula 1 according to claim 1 in which
R1 is methoxy, or ethoxy,
R2 is methoxy, ethoxy, 2,2-difluoroethoxy, or difluoromethoxy,
R3 is hydrogen,
R31 is hydrogen,
R4 is —O—R41, in which
R41 is hydrogen, and
R5 is hydrogen,
R6 is hydrogen,
R7 is bonded to the meta or para position with respect to the binding position in which the phenyl ring is bonded to the phenanthridine ring system, and is a radical of formula (c)

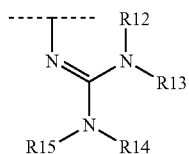

in which
either
R12 is hydrogen,
R13 is hydrogen,
R14 is 1-4C-alkyl, and
R15 is 1-4C-alkyl, or R12 is hydrogen,
R13 is hydrogen,
R14 is hydrogen, and
R15 is 3-5C-cycloalkyl, or R12 is hydrogen,
R13 is hydrogen, and
R14 and R15, together and including the nitrogen atom to which both are bonded, are a azocan-1-yl or a piperazin-1-yl radical substituted in 4-position by R19, in which
R19 is 1-4C-alkylcarbonyl, or a salt, N-oxide, salt of the N-oxide, enantiomer, salt of the enantiomer, E/Z isomer, salt of the E/Z isomer, tautomer or salt of the tautomer thereof.

6. A compound of formula 1 according to claim 1 in which
R1 is methoxy,
R2 is methoxy, ethoxy, difluoromethoxy, or 2,2-difluoroethoxy,
R3 is hydrogen,
R31 is hydrogen,
R4 is —O—R41, in which
R41 is hydrogen, and
R5 is hydrogen,
R6 is hydrogen,
R7 is bonded to the meta or para position with respect to the binding position in which the phenyl ring is bonded to the phenanthridine ring system, and is a radical of formula (c)

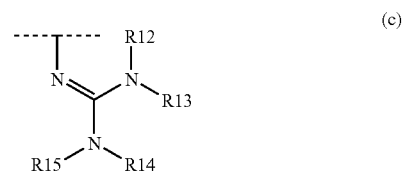

in which
either
R12 is hydrogen,
R13 is hydrogen,
R14 is ethyl, and
R15 is ethyl, or R12 is hydrogen,
R13 is hydrogen,
R14 is hydrogen, and
R15 is cyclopropyl, or R12 is hydrogen,
R13 is hydrogen, and
R14 and R15, together and including the nitrogen atom to which both are bonded, are an azocan-1-yl radical, or a piperazin-1-yl radical substituted in 4-position by R19, in which
R19 is acetyl, or a salt, N-oxide, salt of the N-oxide, enantiomer, salt of the enantiomer, E/Z isomer, salt of the E/Z isomer, tautomer or salt of the tautomer thereof.

7. A compound of formula 1 according to claim 1 selected from the group consisting of 1. N'-(1-{4-[(2RS,4aRS,10bRS)-9-(1,1-Difluoro-methoxy)-2-hydroxy-8-methoxy-1,2,3,4,4a,10b-hexahydro-phenanthridin-6-yl]-phenyl}-methanoyl)-N,N-diethyl-guanidine, 2. N-(1-Amino-1-azocan-1-yl-methylene)-4-[(2RS,4aRS,10bRS)-9-(1,1-difluoro-methoxy)-2-hydroxy-8-methoxy-1,2,3,4,4a,10b-hexahydro-phenanthridin-6-yl]-benzamide, 3. N-Cyclopropyl-N'-(1-{4-[(2RS,4aRS,10bRS)-9-(1,1-difluoro-methoxy)-2-hydroxy-8-methoxy-1,2,3,4,4a,10b-hexahydro-phenanthridin-6-yl]-phenyl}-methanoyl)-guanidine, 4. N-[1-(4-Acetyl-piperazin-1-yl)-1-amino-methylene]-4-((2RS,4aRS,10bRS)-2-hydroxy-8,9-dimethoxy-1,2,3,4,4a,10b-hexahydro-phenanthridin-6-yl)-benzamide, 5. N,N-Diethyl-N'-{1-[4-((2RS,4aRS,10bRS)-2-hydroxy-8,9-dimethoxy-1,2,3,4,4a,10b-hexahydro-phenanthridin-6-yl)-phenyl]-methanoyl}-guanidine, 6. N-(1-Amino-1-azocan-1-yl-methylene)-4-((2RS,4aRS,10bRS)-2-hydroxy-8,9-dimethoxy-1,2,3,4,4a,10b-hexahydro-phenanthridin-6-yl)-benzamide, and the salts, N-oxides, salts of the N-oxides, enantiomers, salts of the enantiomers, E/Z isomers, salts of the E/Z isomers, tautomers and salts of the tautomers thereof.

8. A compound of formula 1 according to claim 1, which have with respect to the positions 4a and 10b the configuration shown in formula 1*:

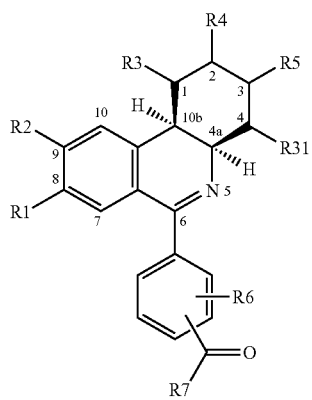

(1*)

or a salt, N-oxide, salt of the N-oxide, enantiomer, salt of the enantiomer, E/Z isomer, salt of the E/Z isomer, tautomer or salt of the tautomer thereof.

9. A compound of formula 1 according to claim 1, which have with respect to the positions 2, 4a and 10b, or, respectively, 3, 4a and 10b the configuration shown either in formula 1a*** or in formula 1b***:

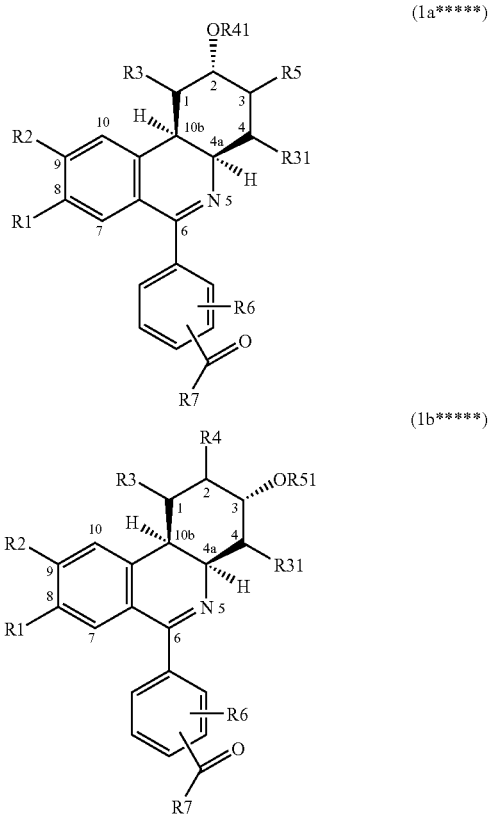

or a salt, N-oxide, salt of the N-oxide, E/Z isomer, salt of the E/Z isomer, tautomer or salt of the tautomer thereof.

10. A pharmaceutical composition comprising one or more compounds of formula 1 according to claim 1, or a pharmaceutically acceptable salt, N-oxide, salt of an N-oxide, enantiomer, salt of an enantiomer, E/Z isomer, salt of an E/Z isomer, tautomer or salt of a tautomer thereof, together with a pharmaceutically acceptable excipient, diluent and/or vehicle.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
gccagcgtgc aaataatgaa gg                    22

<210> SEQ ID NO 2
<211> LENGTH: 21
<212> TYPE: DNA
<213> ORGANISM: Homo sapiens

<400> SEQUENCE: 2 agaggggat tatgtatcca c                     21